(12) United States Patent
Meyer et al.

(10) Patent No.: US 12,128,165 B2
(45) Date of Patent: Oct. 29, 2024

(54) DUAL STAGE DEGASSER

(71) Applicant: MOZARC MEDICAL US LLC, Minneapolis, MN (US)

(72) Inventors: Thomas E Meyer, Minneapolis, MN (US); Calvin P. Verlette, Minneapolis, MN (US); Ishtiaque Masud, Minneapolis, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 535 days.

(21) Appl. No.: 17/236,242

(22) Filed: Apr. 21, 2021

(65) Prior Publication Data
US 2021/0330872 A1 Oct. 28, 2021

Related U.S. Application Data

(60) Provisional application No. 63/015,721, filed on Apr. 27, 2020.

(51) Int. Cl.
| | |
|---|---|
| *B01D 19/00* | (2006.01) |
| *A61M 1/16* | (2006.01) |
| *A61M 1/26* | (2006.01) |
| *A61M 1/34* | (2006.01) |

(52) U.S. Cl.
CPC .......... *A61M 1/1658* (2013.01); *A61M 1/267* (2014.02); *A61M 1/3413* (2013.01); *B01D 19/00* (2013.01); *B01D 19/0036* (2013.01); *B01D 19/0047* (2013.01); *B01D 19/0063* (2013.01); *A61M 2205/3331* (2013.01); *A61M 2205/3334* (2013.01); *A61M 2205/3368* (2013.01); *A61M 2205/3379* (2013.01); *A61M 2205/36* (2013.01)

(58) Field of Classification Search
CPC . B01D 19/00; B01D 19/0036; B01D 19/0063
See application file for complete search history.

(56) References Cited

U.S. PATENT DOCUMENTS

| | | |
|---|---|---|
| 1,683,723 A | 9/1928 | William |
| 3,091,098 A | 5/1963 | Bowers |
| 3,370,710 A | 2/1968 | Bluemle |
| 3,506,126 A | 4/1970 | Lindsay, Jr. |

(Continued)

FOREIGN PATENT DOCUMENTS

| | | |
|---|---|---|
| CN | 101687070 | 3/2010 |
| CN | 101883594 A | 11/2010 |

(Continued)

OTHER PUBLICATIONS

Written Opinion for App. No. PCT US/2021/028607, dated Aug. 3, 2021.

(Continued)

*Primary Examiner* — Robert A Hopkins

(57) ABSTRACT

Devices, systems, and methods for high capacity degassing of dissolved gases and gas bubbles from fluid such as a dialysate are provided. The devices, systems, and methods can include a degassing vessel with at least two degassing chambers. The fluid can be degassed in a first degassing (Continued)

chamber and recirculated through a second recirculating degassing chamber to remove a desired amount of gas such as carbon dioxide.

19 Claims, 3 Drawing Sheets

(56) References Cited

U.S. PATENT DOCUMENTS

| | | |
|---|---|---|
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,776,819 A | 12/1973 | Williams |
| 3,809,241 A | 5/1974 | Alvine |
| 3,850,835 A | 11/1974 | Marantz |
| 3,884,808 A | 5/1975 | Scott |
| 3,902,490 A | 9/1975 | Jacobsen |
| 3,932,150 A | 1/1976 | Komai |
| 3,939,069 A | 2/1976 | Granger |
| 3,989,622 A | 11/1976 | Marantz |
| 4,060,485 A | 11/1977 | Eaton |
| 4,094,775 A | 6/1978 | Mueller |
| 4,136,708 A | 1/1979 | Cosentino |
| 4,142,845 A | 3/1979 | Lepp |
| 4,201,555 A | 5/1980 | Tkach |
| 4,209,392 A | 6/1980 | Wallace |
| 4,269,708 A | 5/1981 | Bonomini |
| 4,316,725 A | 2/1982 | Hovind |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,739,492 A | 4/1988 | Cochran |
| 4,747,822 A | 5/1988 | Peabody |
| 4,750,494 A | 6/1988 | King |
| 4,816,162 A | 3/1989 | Rosskopf et al. |
| 4,826,663 A | 5/1989 | Alberti |
| 4,828,693 A | 5/1989 | Lindsay |
| 4,885,001 A | 12/1989 | Leppert |
| 4,900,308 A | 2/1990 | Verkaart |
| 4,915,713 A | 4/1990 | Buzza |
| 4,950,230 A | 8/1990 | Kendell |
| 4,977,888 A | 12/1990 | Rietter |
| 5,015,388 A | 5/1991 | Pusineri |
| 5,032,265 A | 7/1991 | Jha |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,141,493 A | 8/1992 | Jacobsen |
| 5,180,403 A | 1/1993 | Kogure |
| 5,192,132 A | 3/1993 | Pelensky |
| 5,203,890 A | 4/1993 | Tatsuo |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,419,347 A | 5/1995 | Carruth |
| 5,441,049 A | 8/1995 | Masano |
| 5,442,969 A | 8/1995 | Troutner |
| 5,468,388 A | 11/1995 | Goddard |
| 5,507,723 A | 4/1996 | Keshaviah |
| 5,518,623 A | 5/1996 | Keshaviah |
| 5,591,344 A | 1/1997 | Kenley |
| 5,643,201 A | 7/1997 | Peabody |
| 5,662,806 A | 9/1997 | Keshaviah et al. |
| 5,683,432 A | 11/1997 | Goedeke |
| 5,685,835 A | 11/1997 | Brugger |
| 5,685,988 A | 11/1997 | Malchesky |
| 5,702,536 A | 12/1997 | Carruth |
| 5,744,031 A | 4/1998 | Bene |
| 5,762,782 A | 6/1998 | Kenley |
| 5,849,179 A | 12/1998 | Emerson |
| 5,858,186 A | 1/1999 | Glass |
| 5,863,421 A | 1/1999 | Peter |
| 5,938,938 A | 8/1999 | Bosetto |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,251,167 B1 | 6/2001 | Berson |
| 6,254,567 B1 | 7/2001 | Treu |
| 6,264,680 B1 | 7/2001 | Ash |
| 6,321,101 B1 | 11/2001 | Holmstrom |
| 6,355,161 B1 | 3/2002 | Shah |
| 6,362,591 B1 | 3/2002 | Moberg |
| 6,363,279 B1 | 3/2002 | Ben-Haim |
| 6,521,184 B1 | 2/2003 | Edgson et al. |
| 6,554,798 B1 | 4/2003 | Mann |
| 6,555,986 B2 | 4/2003 | Moberg |
| 6,589,229 B1 | 7/2003 | Connelly |
| 6,593,747 B2 | 7/2003 | Puskas |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,711,439 B1 | 3/2004 | Bradley |
| 6,719,745 B1 | 4/2004 | Taylor |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,861,266 B1 | 3/2005 | Sternby |
| 6,878,283 B2 | 4/2005 | Thompson |
| 6,960,179 B2 | 11/2005 | Gura |
| 7,023,359 B2 | 4/2006 | Goetz |
| 7,033,498 B2 | 4/2006 | Wong |
| 7,074,332 B2 | 7/2006 | Summerton |
| 7,077,819 B1 | 7/2006 | Goldau |
| 7,097,630 B2 | 8/2006 | Gotch |
| 7,101,519 B2 | 9/2006 | Wong |
| 7,153,693 B2 | 12/2006 | Tajiri |
| 7,169,303 B2 | 1/2007 | Sullivan |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,318,892 B2 | 1/2008 | Connell |
| 7,326,576 B2 | 2/2008 | Womble et al. |
| 7,435,342 B2 | 10/2008 | Tsukamoto |
| 7,488,447 B2 | 2/2009 | Sternby |
| 7,500,958 B2 | 3/2009 | Asbrink |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |

(56) References Cited

U.S. PATENT DOCUMENTS

| | | |
|---|---|---|
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,794,419 B2 | 9/2010 | Paolini |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,137,553 B2 | 3/2012 | Fulkerson |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland |
| 8,449,656 B2 | 5/2013 | Kuang-Yeu |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 2001/0007931 A1 | 7/2001 | Blatter |
| 2002/0027106 A1 | 3/2002 | Smith |
| 2002/0042561 A1 | 4/2002 | Schulman |
| 2002/0045851 A1 | 4/2002 | Suzuki |
| 2002/0091371 A1 | 7/2002 | Ritter |
| 2002/0104800 A1 | 8/2002 | Collins |
| 2002/0112609 A1 | 8/2002 | Wong |
| 2003/0010717 A1 | 1/2003 | Brugger |
| 2003/0034305 A1 | 2/2003 | Luehmann |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0131332 A1 | 6/2005 | Kelly |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0140916 A1 | 6/2007 | Spiss |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084718 A1 | 4/2009 | Prisco |
| 2009/0084721 A1 | 4/2009 | Yardimci |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |

(56) References Cited

U.S. PATENT DOCUMENTS

| | | |
|---|---|---|
| 2009/0107335 A1 | 4/2009 | Wilt |
| 2009/0120864 A1 | 5/2009 | Fulkerson |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0102190 A1 | 4/2010 | Zhu et al. |
| 2010/0114012 A1 | 5/2010 | Sandford et al. |
| 2010/0312172 A1 | 12/2010 | Hoffman |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0168017 A1 | 7/2011 | Lamers |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0249916 A1 | 10/2011 | Herrenbauer |
| 2011/0272337 A1 | 11/2011 | Palmer |
| 2011/0284377 A1 | 11/2011 | Rohde |
| 2011/0297593 A1 | 12/2011 | Kelly |
| 2011/0315611 A1 | 12/2011 | Fulkerson |
| 2011/0315632 A1 | 12/2011 | Freije |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0199205 A1 | 8/2012 | Eyrard |
| 2012/0220528 A1 | 8/2012 | VanAntwerp |
| 2012/0220926 A1 | 8/2012 | Soykan |
| 2012/0248017 A1 | 10/2012 | Beiriger |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0001165 A1 | 1/2013 | Pohlmeier |
| 2013/0015302 A1 | 1/2013 | Rter |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0062265 A1 | 3/2013 | Balschat |
| 2013/0168316 A1 | 7/2013 | Noguchi |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2014/0251908 A1 | 9/2014 | Ding |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |
| 2017/0021079 A1 | 1/2017 | Lura |
| 2017/0274129 A1 | 9/2017 | Meyer |

(56) References Cited

U.S. PATENT DOCUMENTS

| | | |
|---|---|---|
| 2017/0281847 A1 | 10/2017 | Venkatesh |
| 2019/0321755 A1 | 10/2019 | Tamura |

FOREIGN PATENT DOCUMENTS

| | | | |
|---|---|---|---|
| CN | 102307650 | 1/2012 | |
| CN | 202105667 | 1/2012 | |
| CN | 101237918 | 1/2013 | |
| CN | 103037917 | 4/2013 | |
| CN | 101883584 | 7/2013 | |
| CN | 103209721 | 7/2013 | |
| CN | 103889481 A1 | 6/2014 | |
| CN | 103957960 | 7/2014 | |
| CN | 204033885 | 12/2014 | |
| CN | 205969911 U * | 2/2017 | |
| CN | 206930512 U * | 1/2018 | ............... G01N 1/34 |
| CN | 208660440 U * | 3/2019 | |
| DE | 3215003 | 4/1985 | |
| DE | 102009031106 | 12/2010 | |
| DE | 102011052188 | 1/2013 | |
| EP | 0022370 A1 | 1/1981 | |
| EP | 0187109 | 7/1986 | |
| EP | 0266795 A2 | 11/1987 | |
| EP | 0264695 | 4/1988 | |
| EP | 0298587 | 6/1994 | |
| EP | 0743071 | 11/1996 | |
| EP | 1175238 | 11/2000 | |
| EP | 1085295 | 11/2001 | |
| EP | 711182 B1 | 6/2003 | |
| EP | 2308526 | 10/2003 | |
| EP | 1364666 A1 | 11/2003 | |
| EP | 1523347 | 1/2004 | |
| EP | 1523350 | 1/2004 | |
| EP | 0906768 B1 | 2/2004 | |
| EP | 1691863 | 4/2005 | |
| EP | 2116269 | 2/2008 | |
| EP | 1450879 | 10/2008 | |
| EP | 1514562 | 4/2009 | |
| EP | 2219703 | 5/2009 | |
| EP | 1592494 B1 | 6/2009 | |
| EP | 1490129 | 9/2009 | |
| EP | 2398529 | 11/2010 | |
| EP | 2575827 A2 | 12/2010 | |
| EP | 2100553 | 8/2011 | |
| EP | 2388030 | 11/2011 | |
| EP | 2576453 A2 | 12/2011 | |
| EP | 2701580 | 11/2012 | |
| EP | 2701595 | 11/2012 | |
| EP | 1545652 B1 | 1/2013 | |
| EP | 1345856 B1 | 3/2013 | |
| EP | 2344220 B1 | 4/2013 | |
| EP | 1351756 | 7/2013 | |
| EP | 2190498 | 7/2013 | |
| EP | 1414543 | 9/2013 | |
| EP | 2701596 | 3/2014 | |
| EP | 2735322 | 5/2014 | |
| EP | 2740502 | 6/2014 | |
| EP | 2883558 | 6/2015 | |
| EP | 1787666 | 11/2015 | |
| EP | 3560572 | 10/2019 | |
| FR | 2237639 | 2/1977 | |
| GB | 638198 | 5/1950 | |
| GB | 2479130 | 5/2011 | |
| JP | 60-132606 | 7/1985 | |
| JP | 60135064 | 7/1985 | |
| JP | 08504116 | 5/1996 | |
| JP | 8173953 A * | 7/1996 | |
| JP | 2002306904 | 10/2002 | |
| JP | 2006325668 A | 12/2006 | |
| JP | 5-99464 | 10/2012 | |
| JP | 2013521862 | 6/2013 | |
| WO | 9532010 A1 | 11/1995 | |
| WO | 1996040313 | 12/1996 | |
| WO | 9937342 | 7/1999 | |
| WO | PCT1124599 | 5/2000 | |
| WO | 0057935 | 10/2000 | |
| WO | 200066197 A1 | 11/2000 | |
| WO | 2000066197 | 11/2000 | |
| WO | 200170307 A1 | 9/2001 | |
| WO | 2001085295 A2 | 9/2001 | |
| WO | 0185295 A2 | 11/2001 | |
| WO | 2002043859 | 6/2002 | |
| WO | 2003043677 A2 | 5/2003 | |
| WO | 2003043680 | 5/2003 | |
| WO | 2003051422 A2 | 6/2003 | |
| WO | 2004008826 | 1/2004 | |
| WO | 2004009156 | 1/2004 | |
| WO | 2004030716 A2 | 4/2004 | |
| WO | 2004030717 A2 | 4/2004 | |
| WO | 2004064616 A2 | 8/2004 | |
| WO | 2004062710 A3 | 10/2004 | |
| WO | 2005044339 | 5/2005 | |
| WO | 2004105589 A3 | 6/2005 | |
| WO | 2005061026 | 7/2005 | |
| WO | 2005123230 | 12/2005 | |
| WO | 2006023589 | 3/2006 | |
| WO | 2006124431 A2 | 11/2006 | |
| WO | 2007010164 A2 | 1/2007 | |
| WO | 2007089855 A2 | 8/2007 | |
| WO | 2007146162 A3 | 12/2007 | |
| WO | 2008037410 | 4/2008 | |
| WO | 2008051994 | 5/2008 | |
| WO | 2009026603 | 12/2008 | |
| WO | 2009024566 | 2/2009 | |
| WO | 2009061608 | 5/2009 | |
| WO | 2009067071 A1 | 5/2009 | |
| WO | WO2009064984 | 5/2009 | |
| WO | 2009071103 | 6/2009 | |
| WO | WO 2009/073567 | 6/2009 | |
| WO | 2009094184 | 7/2009 | |
| WO | 2009132839 A1 | 11/2009 | |
| WO | 2009157877 A1 | 12/2009 | |
| WO | 2009157878 A1 | 12/2009 | |
| WO | 20090157877 | 12/2009 | |
| WO | 2010121820 | 10/2010 | |
| WO | 2011017215 A1 | 2/2011 | |
| WO | 2011025705 A1 | 3/2011 | |
| WO | 2011072337 | 8/2011 | |
| WO | 2011113572 A1 | 9/2011 | |
| WO | WO 2011/112317 | 9/2011 | |
| WO | 2012026978 | 3/2012 | |
| WO | 2012042323 | 4/2012 | |
| WO | 2012050781 | 4/2012 | |
| WO | 2012051996 | 4/2012 | |
| WO | 2012067585 | 5/2012 | |
| WO | 2012138604 A2 | 10/2012 | |
| WO | 2012148781 | 11/2012 | |
| WO | 2012148786 | 11/2012 | |
| WO | 2012148789 | 11/2012 | |
| WO | 2012162515 A2 | 11/2012 | |
| WO | 2012172398 | 12/2012 | |
| WO | 2013019179 A1 | 2/2013 | |
| WO | 2013025844 | 2/2013 | |
| WO | 2013027214 | 2/2013 | |
| WO | 2013028809 A2 | 2/2013 | |
| WO | 2013019994 A3 | 4/2013 | |
| WO | 2013103607 A1 | 7/2013 | |
| WO | 2013103906 | 7/2013 | |
| WO | 2013110906 | 8/2013 | |
| WO | 2013110919 | 8/2013 | |
| WO | 2013114063 A1 | 8/2013 | |
| WO | 2013121162 A1 | 8/2013 | |
| WO | 2013140346 | 9/2013 | |
| WO | 2013141896 | 9/2013 | |
| WO | 2013188861 A1 | 12/2013 | |
| WO | 14066254 | 5/2014 | |
| WO | 14066255 | 5/2014 | |
| WO | 14077082 | 5/2014 | |
| WO | WO 2014/099631 | 6/2014 | |
| WO | 2014117000 | 7/2014 | |
| WO | 2014121158 A1 | 8/2014 | |
| WO | 2014121162 | 8/2014 | |
| WO | 2014121163 | 8/2014 | |
| WO | 2014121167 | 8/2014 | |

(56) References Cited

FOREIGN PATENT DOCUMENTS

| WO | 2014121169 | 8/2014 |
| WO | WO 2014/159918 | 10/2014 |
| WO | 2015071247 A1 | 5/2015 |
| WO | WO2017001358 | 1/2017 |
| WO | WO2017/019640 A1 | 2/2017 |

OTHER PUBLICATIONS 2017-530641_OA.

[NPL142] Hemametrics, Crit-Line Hematocrit Accuracy, 2003, 1-5, vol. 1, Tech Note No. 11 (Rev. D).

[NPL144] Weissman, S., et al., Hydroxyurea-induced hepatitis in human immunodeficiency virus-positive patients. Clin. Infec. Dis, (Jul. 29, 1999): 223-224.

[NPL146] PCT/US2012/034334, International Search Report, Jul. 6, 2012.

[NPL147] PCT/US2012/034335, International Search Report, Sep. 5, 2012.

[NPL148] PCT/US/2012/034327, International Search Report, Aug. 13, 2013.

[NPL149] PCT/US/2012/034329, International Search Report, Dec. 3, 2012.

[NPL161] EP13182115.9-1651 European Search Report, Feb. 3, 2014.

[NPL162] International Search Report from PCT/US2012/051946 mailed Mar. 4, 2013.

[NPL164] Written Opinion of the International Searching Authority for PCT/US2012/049398 mailed Feb. 25, 2013.

[NPL169] Wang, Fundamentals of intrathoracic impedance monitoring in heart failure, Am. J. Cardiology, 2007, 3G-10G: Suppl.

[NPL16] PCT/US2014/067650 International Search Report Written Opinion mailed Mar. 9, 2015.

[NPL170] Bleyer, et al., Kidney International. Jun. 2006; 69(12):2268-2273.

[NPL172] U.S. Appl. No. 29/446,285, filed Feb. 1, 2013.

[NPL175] Marchant, et. al., In vivo Biocompatibility Studies 1: The Cage Implant System and a Biodegradable Hydrogel, J. Biomed. Mat. Res., 1983, 301-325: 17.

[NPL176] Bleyer, et. al., Sudden and cardiac death rated in hemodialysis patients, Kidney International. 1999, 1553-1559: 55.

[NPL178] PCT/US2012/025711, International Search Report mailed Jul. 4, 2012.

[NPL179] PCT/US2013/020404, International Search Report, Jan. 4, 2013.

[NPL187] PCT/US2012/034333, International Preliminary Report on Patentability, Oct. 29, 2013.

[NPL188] PCT/US2012/034333, International Search Report, Aug. 29, 2012.

[NPL189] PCT/US2012/051011, International Search Report, Jan. 17, 2014.

[NPL197] PCT/US2012/034330, International Preliminary Report on Patentability, Oct. 29, 2013.

[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

[NPL230] Redfield, et al, Restoration of renal response to atrial natriuretic factor in experimental low-output heat failure, Am. J. Physiol., Oct. 1, 1989, R917-923:257.

[NPL231] Rogoza, et. al., Validation of A&D UA-767 device for the self-measurement of blood pressure, Blood Pressure Monitoring, 2000, 227-231, 5(4).

[NPL234] Lima, et. al., An electrochemical sensor based on nanostructure hollandite-type manganese oxide for detection of potassium ion, Sensors, Aug. 24, 2009, 6613-8625, 9.

[NPL235] Maclean, Et, Al., Effects of hindlimb contraction on pressor and muscle interstitial metabolite responses in the cat, J. App. Physiol., 1998, 1583-1592, 85(4).

[NPL237] U.S. Appl. No. 13/757,693, dated Feb. 1, 2013.

[NPL238] PCT Application, PCT/US2013/020404, filed Jan. 4, 2013.

[NPL23] U.S. Appl. No. 13/424,525, published Nov. 1, 2012.

[NPL240] U.S. Appl. No. 13/836,973, filed Mar. 15, 2013.

[NPL241] U.S. Appl. No. 14/259,655, filed Apr. 23, 2014.

[NPL242] U.S. Appl. No. 14/259,589, filed Apr. 23, 2014.

[NPL243] U.S. Appl. No. 13/757,693, filed Jan. 4, 2013.

[NPL244] U.S. Appl. No. 13/836,079, filed Mar. 15, 2013.

[NPL245] U.S. Appl. No. 14/240,129, filed Aug. 22, 2013.

[NPL246] PCT/US2014/014346 International Search Report and Written Opinion.

[NPL247] U.S. Appl. No. 13/835,735, filed Mar. 15, 2013.

[NPL248] PCT/US2014/014345 International Search Report and Written Opinion, mailed May 2014.

[NPL250] U.S. Appl. No. 13/835,735 IDS, filed Jun. 13, 2013.

[NPL264] PCT/US2014/014357 International Search Report and Written Opinion dated May 19, 2014.

[NPL264] PCT/US2014/014357 International Search Report and Written Opinion mailed May 19, 2014.

[NPL268] Ronco et al. 2008, Cardiorenal Syndrome, Journal American College Cardiology, 52:1527-1539, Abstract.

[NPL26] Overgaard, et. al., Activity-induced recovery of excitability in K+-depressed rat soleus muscle, Am. J. P 280: R48-R55, Jan. 1, 2001.

[NPL27] Overgaard. et. al., Relations between excitability and contractility in rate soleusmuscle: role of the Na+—K+ pump and Na+—K—S gradients. Journal of Physiology, 1999, 215-225, 518(1).

[NPL306] Coast, et al. 1990, An approach to Cardiac Arrhythmia analysis Using Hidden Markov Models, IEEE Transactions on Biomedical Engineering. 1990, 37(9):826-835.

[NPL309] Weiner, et. al., Article: Cardiac Function and Cardiovascular Disease in Chronic Kidney Disease, Book: Primer on Kidney Diseases (Author: Greenberg, et al.), 2009,499-505, 5th Ed., Saunders Elsevier, Philadelphia, PA.

[NPL310] U.S. Appl. No. 61/480,532, filed Apr. 29, 2011.

[NPL32] Secemsky, et. al., High prevalence of cardiac autonomic dysfunction and T-wave alternans in dialysis patients. Heart Rhythm, Apr. 2011, 592-598 : vol. 8, No. 4.

[NPL35] Wei, et. al., Fullerene-cryptand coated piezoelectric crystal urea sensor based on urease, Analytica Chimica Acta, 2001,77-85:437.

[NPL376] Gambro AK 96 Dialysis Machine Operators Manual, Dec. 2012. p. 1-140.

[NPL376] Gambro AK 96 Dialysis Machine Operators Manual, Dec. 2012. p. 141-280.

[NPL376] Gambro AK 96 Dialysis Machine Operators Manual, Dec. 2012. p. 281-420.

[NPL376] Gambro AK 96 Dialysis Machine Operators Manual, Dec. 2012. p. 421-534.

[NPL377] European Search Report 12819714.2-1651/2739325 PCT/US2012049398, mailed Jun. 12, 2015.

[NPL378] PCT/US2014/14343 Intl Search Report & Written Opinion, mailed May 9, 2014.

[NPL379] PCT/US2014/014350 International Search Report and Written Opinion mailed May 2014.

[NPL37] U.S. Appl. No. 13/368,225, filed Feb. 7, 2012.

[NPL380] Ep 14746793 Supplementary European Search Report dated Aug. 18, 2016.

[NPL381] Ep 14746791 Supplementary European Search Report mailed Aug. 19, 2016.

[NPL382] Ep 14746799 Supplementary European Seach Report dated Aug. 18, 2016.

[NPL383] Leifer et al., A Study on the Temperature Variation of Rise Velocity for Large Clean Bubbles, J. Atmospheric & Oceanic Tech., vol. 17, pp. 1392-1402, Oct. 2000.

[NPL384] Talaia, Terminal Velocity of a Bubble Rise in a Liquid col. World Acad. of Sci., Engineering & Tech., vol. 28, pp. 264-268, Published Jan. 1, 2007.

[NPL386] The FHN Trial Group. In-Center. Hemodialysis Six Times per Week versus Three Times per Week, New England Journal of Medicine, 2010 Abstract.

[NPL39] PCT/US2012/034332, International Search Report, Jul. 5, 2012.

(56) References Cited

OTHER PUBLICATIONS

[NPL462] Office Action in U.S. Appl. No. 13/757,717 Dated Dec. 26, 2014.
[NPL463] Office Action in U.S. Appl. No. 13/757,709 Dated Jun. 6, 2015.
[NPL464] Office Action in U.S. Appl. No. 13/757,709 Dated Jan. 7, 2016.
[NPL465] Office Action in U.S. Appl. No. 13/757,728 Dated Jan. 8, 2016.
[NPL466] Office Action in U.S. Appl. No. 13/757,728 Dated Aug. 12, 2016.
[NPL467] Office Action in U.S. Appl. No. 13/757,796 Dated Apr. 13, 2015.
[NPL468] Office Action in U.S. Appl. No. 13/757,796 Dated Dec. 21, 2015.
[NPL469] Office Action in U.S. Appl. No. 13/836,538 Dated Aug. 19, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL470] Office Action in U.S. Appl. No. 13/836,538 Dated Jan. 11, 2016.
[NPL471] Office Action in U.S. Appl. No. 13/836,538 Dated Apr. 27, 2016.
[NPL472] Office Action in U.S. Appl. No. 13/757,722 Dated May 19, 2016.
[NPL473] Office Action in U.S. Appl. No. 13/757,709 Dated Jan. 7, 2016.
[NPL474] Office Action in U.S. Appl. No. 13/757,693 Dated Nov. 13, 2015.
[NPL475] Office Action in U.S. Appl. No. 13/757,693 Dated May 23, 2016.
[NPL476] Office Action in U.S. Appl. No. 13/757,709 Dated Jun. 6, 2015.
[NPL47] U.S. Appl. No. 61/480,544. unpublished.
[NPL481] Office Action in U.S. Appl. No. 13/757,794 dated Oct. 21, 2015.
[NPL482] Office Action in U.S. Appl. No. 13/757,794 dated May 2, 2016.
[NPL483] Office Action in U.S. Appl. No. 13/424,525 dated Aug. 11, 2015.
[NPL484] Office Action in U.S. Appl. No. 13/424,525 dated Feb. 25, 2016.
[NPL485] Office Action in U.S. Appl. No. 13/424,525 dated Jun. 17, 2016.
[NPL486] Office Action in U.S. Appl. No. 13/424,525 dated Oct. 20, 2016.
[NPL487] Office Action in U.S. Appl. No. 13/424,479 dated Nov. 24, 2014.
[NPL488] Office Action in U.S. Appl. No. 14/566,686 dated Apr. 28, 2016.
[NPL489] Office Action in U.S. Appl. No. 13/424,533 dated Oct. 22, 2013.
[NPL490] Office Action in U.S. Appl. No. 13/424,533 dated Apr. 18, 2014.
[NPL491] Office Action in U.S. Appl. No. 13/424,533 dated Jan. 5, 2015.
[NPL492] Office Action in U.S. Appl. No. 13/424,533 dated Jun. 2, 2015.
[NPL493] Office Action in U.S. Appl. No. 13/424,533 dated Jul. 14, 2016.
[NPL496] Welgemoed, T.J., Capacitive Deionization Technology: An Alternative to desalination Solution, Desalination 183 (2005) 327-340.
[NPL497] European Search Report for App. No. 15193645.7, dated Apr. 15, 2016.
[NPL498] European Search Report in App. No. 15193720.8 dated Apr. 26, 2016.
[NPL499] EP. App. 14746193.3 Search Report dated Oct. 19, 2016.
[NPL528] Office Action in U.S. Appl. No. 14/555,393 Dated May 4, 2016.
CN201510761050.6_Aug. 2, 2017 OA.
European Office Action for App. No. 16757383.1, dated Mar. 13, 2020.
European Office Action for App. No. 17168861.7, dated Jan. 21, 2020.
European Office Action for App. No. 17724468.8, dated May 14, 2020.
European Search Report for App. No. 16760215.0, dated May 7, 2020.
European Search Report for App. No. 17724689.9, dated May 14, 2020.
Extended European Search Report for App. No. 20160568.0, dated Jun. 17, 2020.
Extended European Search Report for App. No. 20203585.3, dated Feb. 17, 2021.
Indian Office Action for App. No. 244/KOLNP/2014, dated Feb. 12, 2020.
Indian Office Action for App. No. 2534/KOLNP/2015, dated Sep. 10, 2020.
Office Action in Chinese App. No. 201580067284.9, dated Oct. 8, 2019.
Office Action in Chinese Application No. 201580067284.9, dated Mar. 6, 2020.
Office Action in European App. No. 19154609.2, dated Mar. 10, 2020.
Office Action in European App. No. 19158804.5, dated Sep. 4, 2020.
Office Action in European App. No. 19219498.3, dated Mar. 26, 2020.
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
[NPL529] Office Action in U.S. Appl. No. 14/555,393 Dated Nov. 1, 2016.
[NPL530] Office Action in U.S. Appl. No. 14/555,414 Dated May 4, 2016.
[NPL531] Office Action in U.S. Appl. No. 14/555,414 Dated Nov. 3, 2016.
[NPL534] Office Action in U.S. Appl. No. 13/586,824 Dated Dec. 21, 2015.
[NPL535] Office Action in U.S. Appl. No. 13/586,824 Dated Jun. 4, 2016.
[NPL546] Office Action in Chinese Application No. 201480007138.2 dated Sep. 28, 2016.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 Dated Jan. 11, 2016.
[NPL559] Office Action in U.S. Appl. No. 13/565,733 Dated Jun. 11, 2015.
[NPL560] Office Action in U.S. Appl. No. 13/586,824 Dated Jun. 4, 2015.

(56) References Cited

OTHER PUBLICATIONS

[NPL561] Office Action in U.S. Appl. No. 13/757,792 Dated Jun. 2, 2016.
[NPL562] Office Action in U.S. Appl. No. 13/757,796 Dated Apr. 13, 2015.
[NPL563] Office Action in U.S. Appl. No. 13/757,796 Dated Dec. 21, 2015.
[NPL564] Office Action in U.S. Appl. No. 13/835,735 Dated Oct. 13, 2015.
[NPL565] Office Action in U.S. Appl. No. 13/836,079 Dated Apr. 17, 2015.
[NPL566] Office Action in U.S. Appl. No. 13/836,079 Dated Jun. 30, 2016.
[NPL569] Office Action in U.S. Appl. No. 13/791,755 Dated Mar. 16, 2016.
[NPL570] Office Action in U.S. Appl. No. 13/791,755 Dated Aug. 9, 2016.
[NPL571] Office Action in U.S. Appl. No. 13/835,735 Dated Jun. 16, 2016.
[NPL572] Office Action in U.S. Appl. No. 13/836,079 Dated Nov. 6, 2015.
[NPL578] Office Action in U.S. Appl. No. 13/791,755 Dated Sep. 10, 2015.
[NPL579] Office Action in U.S. Appl. No. 13/791,755 Dated Apr. 20, 2015.
[NPL580] Office Action in U.S. Appl. No. 14/259,589 Dated Nov. 4, 2016.
[NPL581] Office Action in U.S. Appl. No. 14/261,651 Dated Aug. 25, 2016.
[NPL586] International Search Report from International Application No. PCT/US2014/014347 dated May 9, 2014.
[NPL587] International Search Report for PCT/US2015/060090 date of completion is Feb. 9, 2016 (3 pages).
[NPL592] St. Peter et al., Liver and Kidney Preservation by perfusion, 369 The Lancet 604, 606 (2002).
[NPL593] Office Action for Chinese Application 20148007136.3, Dated Jun. 2, 2016.
[NPL593] Office Action in Chinese Application No. 20148007136.3 dated Jun. 15, 2017.
[NPL594] Office Action for Chinese Application 20148007136.3, Dated Jan. 26, 2017.
[NPL597] Franks, Gene, Cabon Filtration: What it does, What it doesnt, Mar. 14, 2012, pp. 1-3.
[NPL598] PCT/US2014/014352 International Search Report and Written Opinion Jul. 7, 2014.
[NPL599] PCT/US2014/014352 International Prelminary Report on Patentability, Aug. 14, 2015.
[NPL600] Hamm et al,. Sorbent regenerative hemodialysis as a potential cuase of acute hypercapnia, Kidney International, vol. 21, (1982), pp. 416-418.
[NPL624] Office Action in Chinese Application No. 201480007132.5 dated Jul. 19, 2017.
[NPL627] EP Search Report for Application No. 16204175.0 dated Mar. 29, 2017.
[NPL629] Office Action for Chinese Application 201510713880.1 dated Apr. 1, 2017.
[NPL629] Office Action in Chinese Application 201510713880.1 dated Apr. 1, 2017.
[NPL631] Understanding Dialysate Bicarbonate—A simple approach to understanding a complex equation by Fresenius Medical Care, 2011.
[NPL635] International Search Report, Application PCT/US2016/043948, dated Feb. 2, 2017.
[NPL636] Written Opinion, Application PCT/2016/043948, dated Feb. 2, 2017.
[NPL637] International Search Report, Application PCT/US2016/043935, dated Feb. 2, 2017.
[NPL638] Written Opinion, Application PCT/US2016/043935, dated Feb. 2, 2017.
[NPL639] International Search Report and Written Opinion in App. No. PCT/US2012/049398 dated Feb. 25, 2013.
[NPL640] Office Action in European App. No. 12819714.2 dated Aug. 5, 2016.
[NPL641] PCT/US2014/014343 Written Opinion dated Jan. 2, 2015.
[NPL642] PCT/US2014/014343 International Preliminary Search Report dated Mar. 18, 2015.
[NPL643] European Search Report for EP Appl. No. 1474679.4 dated Aug. 19, 2016.
[NPL644] Office Action for Chinese Application 201510761050.6 dated Aug. 2, 2017.
[NPL645] PCT/US2014/014355 International Search Report and Written Opinion dated May 1, 2014.
[NPL646] PCT/US2014/014355 International Preliminary Report dated Apr. 13, 2015.
[NPL647] EP 14746817.7 European Search Report dated Sep. 27, 2016.
[NPL650] Office Action in Chinese Application No. 201480007132.5 dated Feb. 27, 2017.
[NPL652] Office Action in Chinese Application No. 201280047921.2 dated Jun. 11, 2015.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL665] PCT/US2014/014357 International Search Report and Written Opinion dated May 19, 2014.
[NPL666] PCT/US2014/014357 Written Opinion dated Feb. 18, 2015.
[NPL667] European Search Report in European Application No. EP 14746010.9 dated Sep. 15, 2016.
[NPL670] Office Action in European Application No. 14746415.0 dated Apr. 19, 2017.
[NPL67] US Pat. U.S. Appl. No. 13/424,490, published Nov. 1, 2012.
[NPL704] Written Opinion for PCT/US2015/060090 dated Feb. 16, 2016.
[NPL705] Ep 13733819 Supplementary European Search Report dated Jan. 28, 2015.
[NPL713] EP Search Report and Opinion for Application No. 15193720.8 dated May 2, 2016.
[NPL714] Office action for European Application No. 15193720.8 dated Apr. 25, 2017.
[NPL723] PCT/US2012/051011, International Search Report and Written Opinion, Mar. 4, 2013.
[NPL724] Office Action for European Application No. 14746611.4 dated Jan. 3, 2017.
[NPL725] Supplemental Search Report and Search Opinion for European Application No. 14746611.4 dated Aug. 18, 2016.
[NPL728] Examination Report in Australian Application No. AU2014212135 dated May 25, 2017.
[NPL729] Office Action in Chinese Application No. 201480007138.2 dated May 31, 2017.
[NPL736] Office Action in European Application No. 14746193.3 dated Apr. 19, 2017.
[NPL739] European Office Action in Application No. 14746793.0 dated Apr. 13, 2017.
[NPL743] Examination report in Australian Application No. 2014212141 dated May 26, 2017.
[NPL744] Examination report for Australian Application 2015361083 dated Jul. 20, 2017.

(56) References Cited

OTHER PUBLICATIONS

[NPL750] European Search Report and Search Opinion for European Application EP15193720 dated May 2, 2016.
[NPL751] Office Action in European Application No. 15193720.8 dated Apr. 25, 2017.
[NPL752] International Preliminary Report on Patentability for PCT2015/060090 dated Jun. 13, 2017.
[NPL753] European Search Report for European Application EP 15193830.5 dated May 4, 2016.
[NPL754] Office Action for European Application No. 15193645.7 dated Apr. 21, 2017.
[NPL81] U.S. Appl. No. 61/480,539, filed Apr. 29, 2011.
[NPL84] U.S. Appl. No. 61/480,535, filed Apr. 29, 2011.
[NPL90] Nedelkov, et. al., Design of buffer exchange surfaces and sensor chips for biosensor chip mass spectrometry, Proteomics, 2002, 441-446, 2(4).
AU Examiners Report for Application No. 2017246829, dated Jan. 9, 2021.
Brazilian Search Report for App. No. BR112017012326-6, dated Mar. 13, 2020.
Chinese Office Action for App. No. 201580067284.9, dated Mar. 6, 2020.
Chinese Office Action for App. No. 201680041324.7, dated Jun. 1, 2020.
Chinese Office Action for App. No. 201680041413.1, dated May 28, 2020.
Chinese Office Action for App. No. 201680041414.6, dated Jun. 9, 2020.
Chinese Office Action for App. No. 201680041414.6, dated Oct. 20, 2020.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544, filed Apr. 29, 2011.

\* cited by examiner

DUAL STAGE DEGASSER

FIELD

Devices, systems, and methods for high capacity degassing of dissolved gases and gas bubbles from any fluid used for any purpose are provided. In one non-limiting embodiment, the fluid can be a dialysate for use in dialysis. The devices, systems, and methods can include a degassing vessel with at least two degassing chambers for high capacity degassing of one or more dissolved gases in a fluid. The fluid can be degassed in a first degassing chamber and recirculated through one or more recirculating degassing chambers to remove a desired amount of gas such as carbon dioxide.

BACKGROUND

Degassers are used to remove gases from fluid and/or prevent bubble formation at a liquid-air interface. Carbon dioxide and other gases can enter a fluid during many industrial and healthcare processes. Dissolved gas such as carbon dioxide gas and other gases can then be removed from the fluid. If effective degassing is not implemented, dissolved air and air bubbles can impede the desired process or the functioning of other components within the process or system. In some processes, the chemical reactions within the system or process can generate gas. However, the known gas removal systems may lack the capacity to effectively degas the fluid in the system flow path. The known systems oftentimes cannot actively maintain a partial pressure of a gas within a specified range, and therefore, cannot maintain system parameters dependent upon the amount of dissolved gas, such as pH, within a desired range.

In dialysis, dissolved air and air bubbles can interfere with sensors within the flow path, particularly flow meters, conductivity sensors and blood leak detectors. The dissolved air and air bubbles can also mask a dialyzer and/or microbial filters used within the dialysis system, thereby impeding overall system performance and compromising therapy. The available degassers and gas removal systems often fail to effectively remove dissolved air and air bubbles from the fluid in the system flow path. In sorbent based dialysis, the chemical reactions within a sorbent cartridge can generate additional gas apart from gases already present in the fluid, such as carbon dioxide. Low pH sorbent cartridges, those having a pH less than 5, can be used. Low pH sorbent cartridges can provide for precise dialysate bicarbonate control because nearly all bicarbonate is converted to carbon dioxide, thus enabling the bicarbonate concentration at an outlet of the sorbent cartridge to be known. Further, the amount of bicarbonate to be reinfused into the dialysate becomes the prescribed dialysate bicarbonate. Further, the low pH prevents zirconium bleed into the dialysate. Other pH dependent ion removals, such as sulfates, are enhanced with a low pH sorbent cartridge. A low pH sorbent cartridge produces high amounts of carbon dioxide due to nearly complete conversion of urea and bicarbonate to carbon dioxide as spent dialysate passes through the sorbent cartridge. However, the available dialysis systems oftentimes cannot degas fluid exiting a sorbent cartridge outlet, and in particular a low pH sorbent cartridge outlet, within a specified range given the additional gases created by the sorbent cartridge after processing the dialysate fluid. The available degassers and systems cannot actively maintain a partial pressure of carbon dioxide range in a specified range and cannot maintain a desired pH in a dialyzer downstream of the known degassers. Out of range pH or varying pH outside of a desired specification at a dialyzer inlet can impact the safety of the patient and efficacy of therapy. The known degassers and systems also cannot actively control or manage degassing to avoid deviating from a desired gas partial pressure range. The known degassers and systems lack sensors to control and monitor degassing. The known degassers and systems cannot detect errors or check for errors. The known degassers and systems cannot actively manage degassing, set degassing targets, or measure or track performance. The known degassers and systems oftentimes cannot minimize deviation from desired degassing objectives and cannot ensure that the required goals of the degassing process are achieved in a desirable manner.

As such, degassers and related systems and methods are needed that can degas fluid exiting a process or system or process within a specified range for any type of industrial or healthcare system requiring degassing. In dialysis, systems, devices, and methods are needed that can control the amount of gas in carbon dioxide in a dialysate fluid to a desired range. Devices, systems, and methods for removal of dissolved air and air bubbles that may impede function of the dialysis system are required. Adequate degassing is needed when preparing a fluid such as dialysate when delivered to a patient for a therapy, such as dialysis. Active management and control of degassing of the fluid in the system flow path is required. During operation, devices, systems, and methods that can minimize the impact of gas on overall system performance is required. Devices, systems, and methods that can remove dissolved air and air bubbles that can cause masking of system components such as a dialyzer and/or microbial filters within the dialysis system is required. Devices, systems, and methods that contain sensors for checking and detecting errors in degassing is required. Devices, systems, and methods that can actively control and manage a dialysate pH in a range pH 6.8 to pH 7.6 at a dialyzer inlet is required. Devices, systems, and methods that can actively maintain a desired gas partial range throughout the duration of a process, such as a treatment session is required.

SUMMARY OF THE INVENTION

The first aspect relates to a degasser. In any embodiment, the degasser can have a degassing vessel having a first degassing chamber and one or more recirculating degassing chambers wherein the first degassing chamber can have a first sprayer fluidly connectable to a first fluid path for receiving fluid into the degassing vessel. The first sprayer can be positioned inside the first degassing chamber, and a fluid channel positioned inside the first degassing chamber fluidly connected to the one or more recirculating degassing chambers such that the one or more recirculating degassing chambers has a recirculating outlet positioned in the recirculating degassing chamber for recirculating fluid from the recirculating outlet to a recirculating sprayer positioned inside the recirculating degassing chamber. A vent outlet can be fluidly connected to the recirculating degassing chamber for venting gas, and an exit outlet can be configured to exit fluid out of the recirculating degassing chamber.

In any embodiment, the degasser can have one or more recirculating pumps fluidly connected to the recirculating outlet wherein the one or more recirculating pumps pump fluid to the recirculating sprayer via a recirculation line.

In any embodiment, the degasser can have a heater positioned in the recirculation line or in the first fluid path.

In any embodiment, the degasser can have a temperature sensor positioned in the recirculation line downstream of the heater.

In any embodiment, the degasser can have a gas removal pump fluidly connected to the vent outlet wherein the gas removal pump pumps gas out of the recirculating degassing chamber via exhaust line during degassing.

In any embodiment, the degasser can have a fluid pump fluidly connected to the exit outlet wherein the fluid pump pumps fluid out of the recirculating degassing chamber via an exit line In any embodiment, the degasser can have a tachometer measuring revolutions per minute of any one of the pumps inside the degasser.

In any embodiment, the degasser can have a baffle positioned between the fluid channel and the exit outlet.

In any embodiment, the degasser can have a bypass flow path fluidly connected to the recirculation line and the first sprayer for flowing fluid from the recirculating degassing chamber back to the first degassing chamber.

In any embodiment, the degasser can have a nozzle in the first sprayer that is more restrictive than a nozzle of the recirculating sprayer.

In any embodiment, the degasser can have a nozzle in the first sprayer that is less restrictive than a nozzle of the recirculating sprayer.

In any embodiment, the degasser can have a fluid level sensor positioned to measure a liquid level in the first degassing chamber and the one or more recirculating degassing chambers.

In any embodiment, the degasser can have a fluid level sensor that is a linear array of Hall Effect sensors and a magnetic float.

In any embodiment, the degasser can have a temperature sensor positioned in the first degassing chamber.

In any embodiment, the degasser can have a temperature sensor positioned to measure a temperature in the recirculating degassing chamber.

In any embodiment, the degasser can have at least one pressure sensor; wherein the at least one pressure sensor is configured to determine a headspace pressure of the degassing vessel.

In any embodiment, the degasser can have at least one pressure sensor selected from a pressure sensor, an ambient pressure sensor, a gauge pressure sensor, and combinations thereof.

In any embodiment, the degasser can have at least a second pressure sensor; the second pressure sensor configured to determine a nozzle inlet pressure.

In any embodiment, the degasser can have a control system programmed control the headspace pressure and the nozzle inlet pressure to control a recirculation rate.

In any embodiment, the degasser can have a control system programmed to control the headspace pressure by controlling a gas removal pump, controlling a valve fluidly connecting the gas removal pump to the degassing vessel, or a combination thereof.

In any embodiment, the degasser can have the control system programmed to control the headspace pressure based on a fluid temperature, a fluid flow rate through the dialysate flow path, a recirculation rate, or a dialysate carbon dioxide concentration at an inlet of the degasser.

In any embodiment, the degasser can have a fluid that is a dialysate. The first fluid path can be fluidly connectable to a dialysis machine and an exit outlet vent outlet can be fluidly connected to the dialysate machine downstream of the first fluid path.

In any embodiment, the first degassing chamber and the one or more recirculating degassing chambers can share a common headspace.

In any embodiment, the degasser can have a gas or liquid fluid connection between the first degassing chamber and the one or more recirculating degassing chambers.

The second aspect relates to a method of using the degasser of the first aspect. In any embodiment, the degasser can include a method having the steps of flowing fluid from a fluid flow path through the first sprayer into the first degassing chamber of the degasser and flowing fluid from the first degassing chamber into the recirculating degassing chamber; through the first fluid line and through the recirculating sprayer, and also controlling a headspace pressure in the degassing vessel to remove gas from the fluid.

In any embodiment, the method can have the step of controlling the headspace pressure in the degassing vessel comprises the steps of controlling the gas removal pump, controlling a valve connecting the gas removal pump to the recirculating degassing chamber, or a combination thereof.

In any embodiment, the method can have a headspace pressure that is controlled based on a dialysate temperature, a dialysate flow rate through the dialysate flow path, a recirculation rate, and a dialysate carbon dioxide concentration.

In any embodiment, the method can have the step of heating the dialysate in the first fluid line.

In any embodiment, the method can have the step of controlling at least one pump in the first fluid line and at least one pump in the dialysate flow path to set a recirculation rate higher than a dialysate flow rate.

In any embodiment, the method can have the step wherein the recirculation rate is set based on the dialysate flow rate to maintain a set fluid pressure differential across the first sprayer and the recirculating sprayer.

In any embodiment, the method can include a step wherein the recirculation rate is controlled based on a fixed offset to a degas vessel headspace pressure determined based on a set point dialysate flow rate using a look-up table.

In any embodiment, the fluid of the method can be dialysate.

In any embodiment, the method can include a step of determining a fluid pressure at an inlet of the first sprayer and/or the recirculating sprayer with a pressure sensor.

In any embodiment, the recirculation rate can be controlled based on a fluid pressure at an inlet of the first sprayer and/or the recirculating sprayer and a pressure at an outlet of the first sprayer and/or recirculating sprayer The features disclosed as being part of the second aspect can be in the first aspect either alone or in combination, or follow any arrangement or permutation of any one or more of the described elements. Similarly, any features disclosed as being part of the first aspect can be in the second aspect either alone or in combination, or follow any arrangement or permutation of any one or more of the described elements.

DETAILED DESCRIPTION

Figure 1A:
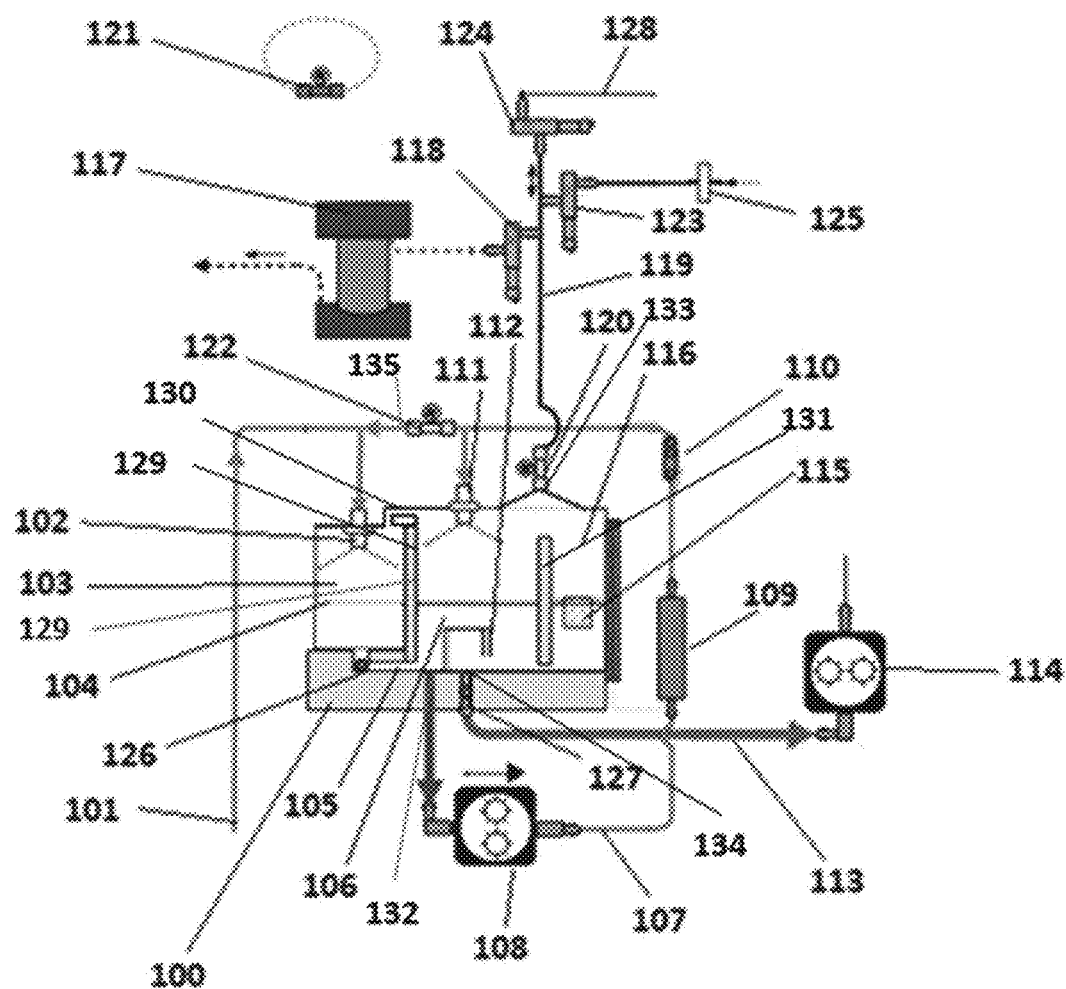
FIG. 1A illustrates a dual stage degassing system.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

An "ambient pressure sensor" is a pressure sensor positioned to measure a pressure outside of a container, system, or fluid path or line, such as atmospheric pressure.

The phrase "at least a" refers to a minimum of the referenced component or feature where additional numbers of duplication of the same A "baffle" is a component that causes partial obstruction of fluid movement.

The phrase "based on" generally means using one or more inputs to add, delete, update, or change in any way another one or more, or same, variable or parameter due to, or because of, the one or more inputs.

A "channel" is a conduit or passageway through which a fluid can travel.

The term "comprising" includes, but is not limited to, whatever follows the word "comprising." Use of the term indicates the listed elements are required or mandatory but that other elements are optional and may be present.

The term "concentration" of any solute such as glucose, icodextrin, amino acid, carbon dioxide, or any other solute, and can refer to the quantity of that solute present in a given quantity of solution.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" can refer to the ability of one component to direct the actions of a second component.

A "control system" is a device which monitors and affects the operational conditions of a given system. The operational conditions are typically referred to as output variables of the system wherein the output variables can be affected by adjusting certain input variables.

The term "dialysis machine" can refer to any machine, device, or system for performing dialysis of any type.

A "degasser" refers to any device, component, or system that can be used to remove one or more gases from a fluid.

A "degassing chamber" is a chamber or other portion of a degassing vessel in which gases can be removed from a fluid.

A "degassing system" is a set of components that are capable of removing dissolved and undissolved gasses from fluids.

A "degassing vessel" or a "degas vessel" is a component of a degasser and can be any structure having an inlet through which fluid enters the vessel, a first outlet through which gas removed from the fluid may pass, and a second outlet through which fluid can exit the vessel. The degassing vessel can have any number of degassing chambers, as defined herein.

The terms "determining," "determines," and the like, generally refer to, in the broadest reasonable interpretation, any process or method for obtaining or coming to a decision, value, number, or finding, for any one or more value, output, parameter, or variable, by any means applicable to the relevant parameter being determined.

The term "dialysate" refers to any mixture that provides for passing solutes of any type through a membrane of any type. Typically, a dialysate contains a concentration of solutes to exchange solutes across a gradient to and from the dialysate during dialysis therapy.

The term "dialysate carbon dioxide concentration" can refer to any measure of an amount of carbon dioxide dissolved in a volume of dialysate.

The term "dialysate flow path" refers to any portion of a fluid pathway that conveys a dialysate and is configured to form at least part of a fluid circuit for hemodialysis, hemofiltration, ultrafiltration, hemodiafiltration or ultrafiltration. Optionally, the fluid pathway can contain priming fluid during a priming step or cleaning fluid during a cleaning step.

The term "dialysate flow rate" refers to a volume of a dialysate moved per unit time.

The term "downstream" refers to a position of a first component in a flow path relative to a second component wherein fluid, gas, or combinations thereof, will pass by the second component prior to the first component during normal operation. The first component can be said to be "downstream" of the second component, while the second component is "upstream" of the first component.

The term "exhaust line" refers to a passageway for removing gas out of a chamber. However, the exhaust line can optionally remove fluid and combinations of gas and fluid. The exhaust line can also provide a means for ingress of gas, fluid, and combinations thereof, depending on the direction of flow and the desired operation, e.g., disinfection and cleaning.

The term "exit line" refers to a fluid passageway for removing fluid out of a chamber. However, the exit line can optionally remove gas and combinations of gas and fluid. The exit line can also provide a means for ingress of gas, fluid, and combinations thereof, depending on the direction of flow and the desired operation, e.g., disinfection and cleaning.

The phrase "exiting fluid" refers to the process of flowing fluid from a chamber, device, component, or system.

The term "exit outlet" refers to an opening that generally provides for removing fluid out of a chamber. However, the exit outlet can optionally exhaust gas and combinations of gas and fluid. The exit outlet can also provide a means for ingress of gas, fluid, and combinations thereof, depending on the flow of fluid and depending the desired operation, e.g., disinfection and cleaning.

The terms "for fluid movement," or to "for fluid movement" refer to providing for fluid to pass in a specified pathway.

The term "flowing" or to "flow" refers to moving a fluid, gas, or combinations thereof in a pathway.

A "fluid level sensor" is a component capable of determining the level of a fluid in a container.

A "fluid path" of "fluid line" can refer to a tubing or conduit through which a fluid, gas, or a combination thereof can pass. The fluid path or line can also contain air during different modes of operation such as cleaning or purging of a path or line.

The term "fluid temperature" refers to the temperature of a fluid in a system, flow path, or component.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type. Notably, the components that are fluidly connectable, need not be a part of a structure. For example, an outlet "fluidly connectable" to a gas removal pump does not require the gas removal pump, but merely that the outlet has the features suitable for fluid connection to the gas removal pump.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

The term "fluid pressure" refers to a force exerted by a fluid within a conduit, container, or component.

The term "fluid pressure differential" refers to a difference in fluid pressure at a first position and at a second position.

The term "gas or liquid fluid connection" refers to a connector, fluid line, or pathway that provides for the movement of gas or liquid.

The term "gas removal" pump refers to a pump of any type for removing a gas.

Optionally, the gas removal pump can remove combinations of gas and fluid, or fluid depending on the procedure being performed, i.e., priming, cleaning.

The term "gauge pressure" refers to pressure within a component measured with respect to ambient pressure.

A "gauge pressure sensor" is a pressure sensor configured to determine a pressure difference between an ambient pressure and a pressure within a component.

A "Hall Effect" sensor is a component that can measure a magnitude of a magnetic field. In certain embodiments, the output voltage of the Hall Effect sensor is directly proportional to a magnetic field strength sensed by the sensor.

The term "headspace" refers to a space above a surface of a fluid to a top surface of a chamber.

The term "headspace pressure" refers to a gas pressure in a headspace portion of a degassing vessel, as defined herein, that can be occupied by gases.

A "heater" is a component capable of raising the temperature of a substance, container, or fluid.

The term "heating" or to "heat" refers to raising the temperature of a substance, container, or fluid.

An "inlet" is a portion of a component through which gas, fluid, and combinations thereof can enter or exit the component. Although the term inlet generally refers to an opening for entry of gas, fluid, and combinations thereof, the inlet can sometimes provide a means for exiting or exhausting the gas, fluid, and combinations thereof. For example, during a priming, cleaning, or disinfection, the inlet can be used to remove gas, fluid, and combinations thereof through the inlet. Also, during operation, the inlet can remove gas, fluid, and combinations thereof.

The term "inside" refers to inner side or surface of any component, chamber, vessel, system. The term is to be used in the broadest reasonable interpretation.

The phrase "less restrictive" as applied to the spray nozzle can refer to a relative change in orifice size, orifice shape, or by any other known technique that can reduce impedance of flow through the nozzle.

The term "lookup table" can refer to a data storage system or configuration such as an array that provides for retrieval and indexing of data of any type.

A "magnetic float" can refer to a type of fluid level sensor having a magnetism or an electrical charge that can be detected to measure the level of fluids. Often, magnetic floats are used with Hall Effect sensors to measure a fluid level in a defined liquid column.

The term "measure a liquid level" refers to determining a height of a liquid within a vessel, container, or chamber.

The term "measure a temperature" refers to determining a temperature of a substance or space.

The term "measuring chamber" refers to a chamber that can contain fluid and gas where a measurement of any type can be taken inside the measuring chamber.

The phrase "more restrictive" as applied to the spray nozzle refers to a relative change in orifice size, orifice shape, or by any other known technique that can impede flow through the nozzle.

The term "nozzle inlet pressure" refers to a fluid pressure of liquid at an entrance of a nozzle.

An "outlet" is a portion of a component through which gas, fluid, and combinations thereof can enter or exit the component. Although the term outlet generally refers to an opening for egress or exhausting of gas, fluid, and combinations thereof, the outlet can sometimes provide a means for entry of a gas, fluid, and combinations thereof. For example, during a priming, cleaning, or disinfection, the outlet can be used to backflush fluid through the outlet. Also, during operation, the outlet can also provide for re-entry of gas, fluid, and combinations thereof.

The term "positioned" refers to a component connected to or in contact with the feature being referred to. The contact can be physical, fluid, or electrical and is intended to be used in the broadest reasonable interpretation.

The term "pressure sensor" refers to a device for measuring the pressure of a gas, a fluid, or a combination thereof in a vessel, container, or fluid path.

The term "programmed," when referring to a processor, can mean a series of instructions that cause a processor to perform certain steps.

A "pump" is a device that causes the movement of fluids or gases through a flow path by applying suction or pressure.

The terms "recirculating," "recirculation," and the like refer to the process or method of circulating anything again through the same component, device, or system.

The term "recirculating degassing chamber" refers to a degassing chamber that can recirculate fluid, gas, and combinations thereof inside the same chamber.

The term "recirculation line" refers to a flow path or fluid passageway of any type that can be used to recirculate fluid, gas, and combinations thereof back into a same component, chamber, device, or system.

The term "recirculating pump" refers to a pump that can be used to recirculate fluid, gas, and combinations thereof back into a same component, chamber, device, or system.

The term "recirculation rate" refers to a volume of fluid recirculated back to a starting position per unit of time.

The term "recirculating outlet" refers to an opening that provide a means for egress of a fluid, gas, and combinations thereof, during an operation. However, the outlet can also provide a means for ingress depending on the flow of fluid and depending the desired operation.

The term "recirculating sprayer" refers to a sprayer that can optionally spray recirculated fluid, gas, and combinations thereof.

The terms "removing gas" or to "remove gas" from a fluid can refer to causing gases to come out of solution in the fluid or to removing bubbles from a fluid.

The term "restrictive" refers to a force exerted by a component resisting the movement of a fluid or gas.

The term "Revolutions Per Minute," or RPM refers to a number of turns in one minute and is a unit of rotational speed or the frequency of rotation around a fixed axis.

A "sensor" is any component capable of determining one or more states of one or more variables in a system The term "setting," "set," or "to set" in the context of performing a series of instructions or steps refers to the process of adjusting or controlling one or more variable to a desired value for use in a process, method, or system.

The phrase "share a common headspace" refers to two or more chambers fluidly connected at a level above a liquid level within the chambers such that gases can pass between the two or more chambers.

A "sprayer" is a component that can atomize or increase the surface area to volume ratio of a fluid.

A "tachometer" refers to an instrument that can measure the rotational speed of a shaft or disk, as in a motor or other machine. In particular, the tachometer can measure the revolutions of minutes of any of the rotational pumps.

The term "temperature sensor" refers to a device for measuring the temperature of a fluid, a gas, or a combination thereof in a vessel, container, or fluid path.

The term "top portion" refers to the portion of a component at a height higher than the center of a component when positioned for normal use.

A "valve" is a device capable of directing the flow of fluid, gas, or a combination thereof, by opening, closing or obstructing one or more pathways to flow the fluid, gas, or combination thereof to travel in a particular path. One or more valves configured to accomplish a desired flow can be configured into a "valve assembly."

The phrase "venting gas" refers to the process of releasing gas from a chamber, device, component, or system.

The term "vent outlet" refers to an opening that generally provides for exhausting gas out of a chamber. However, the vent outlet can optionally exhaust fluid and combinations of gas and fluid. The vent outlet can also provide a means for ingress of gas, fluid, and combinations thereof, depending on the flow of fluid and depending the desired operation, e.g., disinfection and cleaning.

Multiple Stage Degassing

The degasser, degassing systems, and degassing methods can be used in any system requiring the removal of gas from a fluid and/or to prevent bubble formation at a liquid-air interface. The figures herein illustrate the degasser, degassing systems, and degassing methods for use in a dialysis system for removing carbon dioxide from a dialysate. However, the degasser, degassing systems, and degassing methods can be used in any type of system or process for gas removal wherein the exemplification of a dialysate system is just one non-limiting use.

The degassers can have multiple stages for degassing. For example, a multiple stage degasser can have a first degassing chamber and one or more subsequent recirculating chambers for recirculating fluid inside the respective chambers. In other embodiments of multiple stage degassers, the degassing vessels can have a first degassing chamber, one or more recirculating degassing chamber, and a measuring chamber. Alternatively, the multiple stages degasser can have a first degassing chamber, a single recirculating degassing chamber, a third degassing chamber, and a fourth measuring chamber. Still further, the degassing vessel can have a first degassing chamber, a recirculating degassing chamber, a third measuring chamber, and a fourth measuring chamber. Any number, combination, and use of the chambers is contemplated. In any of the multiple stage degassers, fluid inside each of the chambers can be in fluid communication across the first degassing chamber, recirculating degassing chamber, and measuring chamber. During operation, fluid can be recirculated in the recirculating degassing chambers. Each of the recirculating degassing chambers can exhaust gas. The fluid can then be further recirculated in subsequent recirculating degassing chambers. The recirculating degassing chambers can be in gas communication with each other to equilibrate pressures and expel gas from all chambers simultaneously. The degassing chambers can share a common headspace or the degassing vessel can include one or more gas or liquid fluid connections to provide for liquid or gas to pass between degassing chambers. The plural recirculating chambers can also be in fluid communication with each other wherein fluid can be at the same level across all the chambers where the degassing chambers share a mutual gas headspace. Alternatively, each of the recirculating degassing chambers can have separate vents to expel gas separately and/or be isolated from each other. Each of the recirculating degassing chambers can be removed or added to the degassing vessel. In this manner, the multiple stage degasser can be modularized to adjust degassing capacity, as needed. The ability to add or remove one more recirculating degassing chambers to change degassing capacity can be used to customize the multiple stage degassers for a specific degassing requirement.

Dual Stage Degasser

FIG. 1A depicts a dual stage embodiment. In particular, a degassing vessel 100 has a first degassing chamber 103, and one recirculating degassing chamber 106, and a third measuring chamber 116. The dual stage designation refers to the number of chambers performing degassing, i.e., containing a sprayer. As provided herein, the degassing vessel 100 can have more than two degassing chambers.

In FIG. 1A, fluid from a fluid flow path can enter a degassing vessel 100 through a fluid path 101. The fluid path 101 can be fluidly connectable to the degassing vessel 100 to provide for detachment and reattachment of the degassing vessel 100 via the first fluid path 101. For example, the degassing vessel 100 can be reversibly connected to a system such as a hemodialysis machine. The detachment and reattachment can make servicing and replacement of components easier and more convenient. Optionally, the fluid path 101 can be in direct fluid connection to the degassing vessel 100. For example, the degassing vessel 100 can be configured as part of a removable cassette with one or more integrated pumps. The fluid path 101 can be of any length and can be a passageway formed by an outer surface of the degassing vessel 100. If the fluid path 101 is a passageway formed from a material making up the degassing vessel 100, a side of the fluid path 101 can have features to attach and detach the degassing vessel 100 to any other fluid path, component, or system. For example, a luer lock, screw, snap-fitting, or other suitable connection can be integrated into the fluid path 101 for fluid flow into the degassing vessel 100. One of ordinary skill will understand that fluid can flow from any one or more components via fluid flow path 101 into the degassing vessel 100.

Upon entering fluid path 101, fluid can pass through the fluid path 101 to a first sprayer 102 positioned at around a top surface of the first degassing chamber 103. The first sprayer 102 can spray fluid downwardly into a gas headspace of the first degassing chamber 103. The first sprayer 102 can be positioned at a center of the top of the first degassing chamber 103. The top surface can be an interior of first degassing chamber 103 so that the first sprayer 102 can direct spray in the downward direction. Alternatively, the first sprayer 102 can spray the fluid into the first degassing chamber 103 at any angle, including from the bottom of the first degassing chamber 103 towards the top so long as the resulting spray is exposed above the liquid in the first degassing chamber 103. The first sprayer 102 can be positioned on any side or sidewall of the first degassing chamber 103 such that the first sprayer 102 avoids direct fluid contact with a fluid contained inside the first degassing chamber 103. Optionally, two or more sprayers can be used to increase flow and atomization where the sprayers can be positioned at any one or more of the top and sides of the first degassing chamber 103. The first sprayer 102 can create a thin spray or mist to increase release of dissolved gases from solution by increasing the surface area of liquid in contact with the low-pressure atmosphere in the degassing vessel 100. Atomization via first sprayer 102 and/or recirculating sprayer 111 can create a high surface area to volume ratio between liquid droplets and gas in the degassing vessel 100 gas headspace. A high surface area to volume ratio can accelerate gas transport between a liquid and a gas.

The headspace in either the first degassing chamber 103 or the recirculating degassing chamber 106 can be defined as the volume above a surface of the liquid to an inner top surface of the degassing vessel. If all of the first degassing chambers are in gas communication, the headspace can be defined as the volume above a surface of the liquid in all of the chambers of the degassing vessel 100. FIG. 1A shows the first degassing chamber 103 and the recirculating degassing chamber 106 in gas communication such that the gas is equilibrated across both the first degassing chamber 103 and the recirculating degassing chamber 106 with a common headspace. Alternatively, the first degassing chamber 103 and the recirculating degassing chamber 106 can be in gas communication using one or more fluid connectors (not shown). Alternatively, the first degassing chamber 103 and the recirculating degassing chamber 106 can be gas-isolated from each other such that the headspace in the first degassing chamber 103 and the recirculating degassing chamber 106 each define a separate volume and therefore, a separate headspace pressure. Gas-isolation means that the respective chambers do not share a gas headspace and that therefore, pressure does not equilibrate across the chamber. Gas-communication means that the chambers share a gas headspace and pressure equilibrates across the chambers. In gas-isolated embodiments, a pump or valve (not shown) can be included to control liquid flow between chambers. Separate level sensors can be included in each chamber, with the pump or valve controlling liquid flow to maintain appropriate levels in each chamber.

In certain embodiments, the first sprayer 102 and recirculating sprayer 111 can be positioned in a single chamber rather than separate chambers. However, using a single chamber may not provide for driving the outlet gas content to a low level. The headspace pressure can be shared with the third measuring chamber 116 wherein the gas headspace pressure is equilibrated across each of the first degassing chamber 103, recirculating degassing chamber 106, and third measuring chamber 116. The headspace pressure in one or more chambers can contain a vent for exhausting gas. The gas can be controlled to a set-point, absolute pressure target to control fluid exiting the degassing vessel 100 to a partial pressure of a gas within a specified range. In any embodiment, the gas headspace pressure can be monitored across one or more chambers to confirm that degassing is operating within certain tolerances or established limits.

Figure 1B:
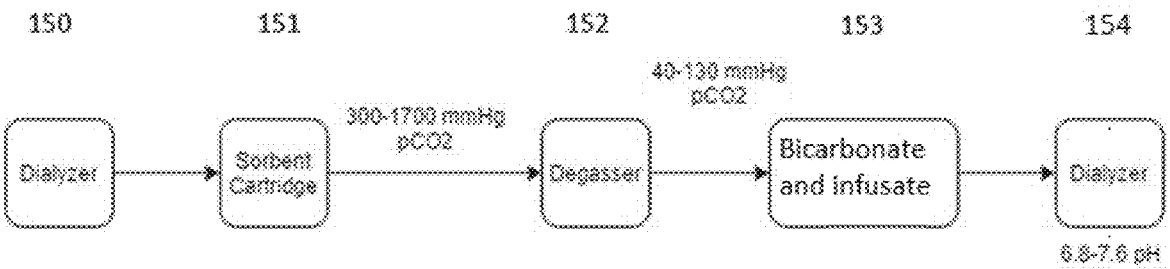
FIG. 1B is a degassing system for use in a dialysis therapy including a dialyzer and a sorbent cartridge.

In sorbent-based dialysis, a specified range partial pressure of a gas exiting the degassing vessel 100 can be based on the bicarbonate concentration of the final dialysate, as more bicarbonate results in a higher pH for a given $CO_2$, as well as the acid content of the cation infusate used. In certain embodiments, the specified $CO_2$ range can be set as 40 mmHg to 130 mmHg $pCO_2$ which can result in a dialysate pH between 6.8 and 7.6 and a carbon dioxide level that will not overwhelm the respiratory system of a patient with cardio respiratory disease. In FIG. 1B, the dialysis system is capable of controlling $CO_2$ removal during a treatment session such that the $CO_2$ concentration in the dialysate flowing out of the degasser is controlled within the range 40 mmHg-130 mmHg $pCO_2$ under the following operating conditions for dialysate flow rate, dialysate temperature, sorbent effluent $CO_2$ concentration, and sorbent effluent dissolved air (dissolved $N_2$, $O_2$). However, the $pCO_2$ at the outlet of the degasser should be appropriate and matched to the bicarbonate and cation infusate such that the final pH is within an acceptable range, and may differ from the range 40 mmHg-130 mmHg $pCO_2$. Dialyzer 150 at an outlet can flow dialysate to a sorbent cartridge 151 to regenerate the dialysate as in REDY (REgeneration of DialYsate) dialysis. In REDY dialysis, sorbents are used to remove solutes and toxins from a used dialysate to purify and reconstitute the dialysate and flow the reconstituted dialysate back to the dialyzer and treat a patient. Recirculating sorbent dialysis machines can use about 500 mL to about 10 L of water per treatment cycle. In those machine and systems, $CO_2$ should be removed to provide for sufficient removal of $CO_2$. However, the fluid should not be removed such that the dialysate is not over-degassed wherein the solution becomes depleted of $CO_2$. After being reconstituted in the sorbent cartridge 151, the partial pressure of $CO_2$ can range from 300-1700 mmHg when using a low pH sorbent cartridge, or lower with a higher pH sorbent cartridge. The degasser 152 can have sufficient capacity to remove $CO_2$ such that the partial pressure of $CO_2$ prior to addition of bicarbonate and cation infusate 153 so that dialysate re-entering the dialyzer 154 is actively controlled as described to result in a target pH range of between 6.8 to 7.6 depending on the requirements of the system and patient. Part of the required capacity of the degasser 152 depends on the dialysate flow rate. A higher flow rate requires a higher capacity degasser as the fluid spends less time in the chamber, while slower flow rates require less capacity as fluid spends more time in the chamber degassing. The range is required to maintain a desired physiological pH of 6.8 to 7.6 in the dialyzer. The degasser 152 can avoid deviation from a nominal dialysate $pCO_2$ of 85 mmHg of fluid exiting the degasser 152.

The degasser 152 can also account for the environmental pressure such as the altitude at which the hemodialysis system is being operated. The dialysis system 150 can be specified to operate at environmental pressures between 700 hPa to 1,060 hPa (at 1500 ft below sea level to 10,000 ft elevation). The concentration of a dissolved gas in a liquid is proportional to the partial pressure (absolute, not gage) of that gas in the headspace above the liquid in the degasser 152 and environmental pressure should be accounted for when controlling the degas vessel headspace pressure in the degasser 152. The dialysate flow rate in the cation dialyzer 153 can be in range from 100 mL/min to 600 mL/min. The dialysate temperature in the cation dialyzer 153 can be in range from 35° C. to 39.5° C.

In FIG. 1A, the first degassing chamber 103 and the recirculating degassing chamber 106 have a shared headspace pressure wherein the chamber wall 129 does not contact the upper interior surface of the degassing vessel 100 to provide for an inter-chamber gas communication channel 130. In the first degassing chamber 103, line 104 represents a top level of liquid in the degassing vessel 100. The fluid can exit the first degassing chamber 103 through a fluid channel 105 positioned at a bottom surface of the first degassing chamber 103 and enter the recirculating degassing chamber 106. Fluid can transfer between the degassing chambers by any other suitable means such as optional fluid channels (not shown) in the chamber wall 129 separating the first degassing chamber 103 and the recirculating degassing chamber 106. Alternatively, a pump or valve can be included to control liquid fluid movement if the headspaces of first degassing chamber 103 and recirculating degassing chamber 106 are separated and/or operate at different pressures. The fluid channel 105 can be a fluid path or line, flow path, or any other type of fluid communication between the first degassing chamber 103 and the recirculating degassing chamber 106. The recirculating degassing chamber 106 can have a recirculating outlet 132 positioned to receive fluid in the recirculating degassing chamber. The fluid can then be recirculated from the recirculating outlet 132 to a recirculating sprayer 111 positioned at a top of an inside surface the recirculating degassing chamber 106. A vent outlet 133 can fluidly connected to recirculating degassing chamber 106 to vent gas. Although shown as positioned at the top surface near recirculating sprayer 111 in FIG. 1A, the vent outlet 133 can be positioned at any location in fluid communication with recirculating degassing chamber 106, including within first degassing chamber 103 if first degassing chamber 103 and recirculating degassing chamber 106 share a headspace. An exit outlet 134 can be positioned to receive fluid that can then be removed from the recirculating degassing chamber 106.

Temperature sensor 126 can be positioned at any location in first degassing chamber 103 to measure the temperature of the fluid contained inside the first degassing chamber 103. For example, the temperature sensor 126 can be positioned at a bottom surface of the first degassing chamber 103. Alternatively, the temperature sensor 126 can be positioned at or near the recirculating outlet 132 or inside or adjacent to fluid channel 105. The temperature of liquid within recirculation line may differ from the temperature within recirculating degassing chamber 106 due to mixing of unheated liquid from first degassing chamber 103 or evaporative cooling. Evaporative cooling occurs as the liquid passes thru the nozzle of the first sprayer 102. The temperature of the liquid is lower after it passes thru the nozzle and is collected in the liquid pool in first degassing chamber 103. The effect of the evaporative cooling can be on order of 1° C. The temperature change can be significant for both degassing control and dialysate temperature control to the dialyzer inlet. As such, a temperature sensor positioned in the recirculating degassing chamber 106 can be used to measure a temperature in the recirculating degassing chamber 106. Fluid channel 105 can provide for fluid movement from the first degassing chamber 103 to the recirculating degassing chamber 106. Fluid can exit the recirculating degassing chamber 106 through the recirculating outlet 132 positioned at around a bottom surface of the recirculating degassing chamber. The recirculating outlet 132 can be in fluid communication with a recirculation line 107, drawn by a recirculating pump 108. Recirculation line 107 can recirculate the fluid inside the recirculating degassing chamber 106. Recirculation line 107 can be fluidly connected to a recirculating sprayer 111 at a top portion of the recirculating degassing chamber 106. Recirculation line 107 can recirculate fluid back into the degassing vessel 100, generally, and into recirculating degassing chamber 106, specifically, to increase an amount of gas removed. In any embodiment, additional degassing chambers can be configured with similar recirculating fluid paths or lines positioned in the degassing chambers for compartmentalized recirculation and degassing such that at least two or more second recirculating degassing chambers are in fluid communication with each other. In that manner, the capacity of the degasser to remove gases can be increased as fluid is recirculated and passed from one recirculating degassing chamber to the next recirculating degassing chamber. Each of the degassing chambers can have a recirculating pump for recirculating fluid back to a sprayer positioned in the respective recirculating degassing chamber to provide high capacity degassing. Each of the additional recirculating degassing chambers can be modular wherein the degassing capacity can be increased or decreased by adding or removing one or more recirculating degassing chambers.

The recirculating sprayer 111 can be positioned at a top of the recirculating degassing chamber 106. Alternatively, the recirculating sprayer 111 can be positioned on any sidewall of the recirculating degassing chamber 106 such that the recirculating sprayer 111 avoids direct fluid contact with a fluid contained inside the recirculating degassing chamber 106. Optionally, two or more sprayers can be used to increase flow and atomization where the sprayers can be positioned at any one or more of the top and sides of the recirculating degassing chamber 106. Recirculating pump 108 can be operated to not only provide fluid recirculation but to also re-introduce the fluid via the recirculating sprayer 111 into the headspace so that dissolved gas in the liquid pool contained in both the first degassing chamber 103 and the recirculating degassing chamber 106 can come into approximate equilibrium with the gas partial pressures in the degas vessel 100 headspace.

Gas bubble nucleation can occur as fluid is sprayed through first sprayer 102 and recirculating sprayer 111 wherein fluid can enter a low pressure gas headspace contained within the first degassing chamber 103 and recirculating degassing chamber 106 via recirculating sprayer 111. Bubbles of undissolved gas can rise through the liquid column in the degassing vessel 100 and be captured and collected in the degassing vessel 100 headspace and exhausted through one or more vents. Bubble capture can be provided if the downward velocity of the liquid column is less than the rise velocity of bubbles through the liquid column. The gas phase pressure in the degassing vessel 100 can be controlled by gas removal pump 117 and valve 118.

The gas removal pump 117 can be a vacuum diaphragm pump or any other suitable pump that moves accumulated gases including carbon dioxide, air, and water vapor from the low pressure headspace in the degassing vessel 100 to atmosphere. The gas removal pump 117 is capable of drawing down the degassing vessel 100 headspace vacuum to approximately 80-100 mmHg absolute when operating at steady state. The gas removal pump 117 maximum gas removal capacity can be ~1.5 standard liters per minute at 100 mmHg absolute degassing vessel 100 headspace pressure. During transitions of emptying and filling the degassing vessel 100, the operation of valve 118 and valve 123 can be performed in a manner that prevents fluid from being forced into air filter 125 and prevents liquid from entering gas removal pump 117.

Generally, valve 118 can be opened during use wherein gas removal pump 117 can withdraw gas via exhaust line 119 from the degassing vessel 100 through vent outlet 133. However, if the gas phase pressure is reduced to a set minimum threshold, valve 118 can be closed, as needed, to result in an increase in gas phase pressure in the degassing vessel 100 to provide for continued exhaust of gas via gas removal pump 117.

The recirculation line 107 can include a heater 109 to heat the fluid to a desired temperature. Temperature sensor 110 can measure the temperature of the heated fluid in recirculation line 107. The desired temperature is controlled such that the dialysate temperature at an inlet of the dialyzer is within a target range. As such, the heater control can account for temperatures measured downstream of the degassing system and set the temperature as measured by temperature sensor 110 to ensure that dialysate at the dialyzer is within a desired range. The heater 109 positioned in recirculation line 107 can lessen a vacuum burden because, according to Henry's law, the concentration of dissolved gas at equilibrium with a gas phase partial pressure increases as temperature decreases. Temperature sensor 110 can be positioned at any location in recirculation line 107 to measure the temperature of the fluid that enters through recirculating sprayer 111. The temperature sensor 110 can be positioned downstream of the heater 109 in the recirculation line 107 to obtain accurate and precise readings of the heated fluid. Optionally, recirculation line 107 can also be fluidly connected to the first sprayer 102 to flow excess fluid back into first degassing chamber 103, lowering the fluid pressure in recirculation line 107 via bypass flow path 135.

Baffle 112 can be positioned at a bottom portion of the recirculating degassing chamber 106. Baffle 112 can prevent fluid from entering exit outlet 134. Baffle 112 slows fluid entering from fluid channel 105 from flowing directly into the exit line 113 by forcing the fluid to travel further to reach the exit line 113 providing for more time for the fluid to degas in the degassing vessel 100 or to be pulled into recirculating outlet 132. Exit line 113 flows degassed fluid out of the degassing vessel 100 wherein baffle 112 helps to ensure fluid is recirculated prior to being flowed out of the degassing vessel 100. Baffle 112 can be constructed into any suitable shape or configuration from any suitable material known by those of skill in the art to direct fluid away from the exit line 113. Baffle 112 can be positioned anywhere in the degassing vessel 100 to prevent liquid from flowing directly from first degassing chamber 103 to exit line 113. Alternatively, exit line 113 can be positioned at a suitable location or distance away from fluid channel 105 wherein fluid from the first degassing chamber 103 is not passed directly back into the dialysate flow path, without first being recirculated into recirculation line 107, and through heater 109 and recirculating sprayer 111. For example, a fluid outlet for exit line 113 can be positioned at an opposite end of the recirculating degassing chamber 106 from fluid channel 105.

Fluid pump 114 can be positioned in exit line 113 to pump fluid out of the recirculating degassing chamber 106. The fluid pump 114 can be a subsequent recirculating pump that recirculates fluid to a third recirculating degassing chamber, or the fluid pump 114 can be used to pump degassed fluid out of the degassing vessel 100. If the pumped fluid is degassed fluid, the degassed fluid can be pumped back into a main process flow path, such as a dialysate flow path downstream of fluid path 101. A temperature sensor 127 can measure the temperature of the fluid exiting through exit line 113. Temperature sensor 127 can be positioned at any location in recirculating degassing chamber 106 to measure the temperature of the liquid pool in recirculating degassing chamber 106 so that the optimal headspace pressure set point can be determined. A lower liquid temperature would result in a lower headspace pressure, and vice versa. The temperature sensor 127 can be positioned at a bottom surface of the recirculating degassing chamber 106. Alternatively, the temperature sensor 127 can be positioned at or near exit outlet 134 or inside or adjacent to the exit line 113.

In certain embodiments, the nozzle of the first sprayer 102 can be more restrictive than the nozzle of the recirculating sprayer 111. In other embodiments, the nozzle of the first sprayer 102 can be less restrictive than the nozzle of the recirculating sprayer 111. Relative nozzle orifice sizing can be employed to balance the relative flows into degassing vessel 100 between a nozzle orifice size of first sprayer 102 and recirculating sprayer 111. The nozzle orifices can be sized to control relative flow through each nozzle to a desired proportion of the total flow. The nozzle can be fabricated by any know configurations, materials, and methods. Plain-orifice nozzles, shaped-orifice nozzles, surface-impingement single-fluid nozzles, pressure-swirl single-fluid spray nozzles, solid-cone single-fluid nozzles, compound nozzle, or any other suitable nozzle known to those of skill in the art are contemplated. Nozzle restrictiveness can be modified by orifice size, orifice shape, or any other known technique. In certain embodiments, the recirculation rate can be set higher than the dialysate flow rate entering the recirculating degassing chamber 106. The more restrictive nozzle of the first sprayer 102 ensures that there is enough flow coming from the recirculating pump 108 to prevent any fluid from bypassing the first degassing chamber 103. An optional bypass flow path 135 can be fluidly connected to the recirculation line 107 and the first sprayer 102 to flow fluid back to the first degassing chamber 103. When optional bypass flow path 135 is used with the first sprayer 102 and recirculating sprayer 111 sharing a common inlet, recirculating pump 108 can control the recirculation pressure according to a setpoint differential between pressure sensor 122 and gauge pressure sensor 120 such that liquid flow thru optional bypass flow path 135 goes only in a single direction towards the inlet of first sprayer 102, according to the direction arrow shown in FIG. 1A. If this flow direction is not controlled, then a fraction of undegassed liquid may pass directly to recirculating sprayer 111 and control of $pCO_2$ may be compromised. If optional bypass flow path 135 is not used, and the first sprayer 102 and recirculating sprayer 111 are separate, the orifices of the nozzles of first sprayer 102 and recirculating sprayer 111 could be sized such that flow into the degassing vessel 100 is balanced without optional bypass flow path 135.

The system can control the liquid level in the degassing vessel 100 to a desired height. A fluid level sensor can be positioned to measure the liquid level in the degassing vessel 100. In certain embodiments, the fluid level sensor can be a linear array of Hall Effect sensors and a fluid level sensor 115 that floats on a liquid level to determine the height of the liquid. One of skill in the art will understand that alternative methods of measuring the liquid level are contemplated such as optical or ultrasonic sensors. In certain embodiments, the fluid level sensor 115 can be positioned in the third measuring chamber 116. The third degassing chamber 113 can be separated from the recirculating degassing chamber 106 by a second chamber wall 131. The recirculating degassing chamber 106 and the third measuring chamber 116 can be in fluid communication. The gas can also be in gas communication between the recirculating degassing chamber 106 and the third measuring chamber 116. The second chamber wall 131 can help avoid the fluid level sensor 115 from being affected by the fluid entering the degassing vessel 100 through either the first sprayer 102 and recirculating sprayer 111. The liquid level can be set below the first sprayer 102 and recirculating sprayer 111 so that the outlets of the first sprayer 102 and recirculating sprayer 111 are exposed and atomized dialysate exiting the spray nozzle is exposed to the low pressure gas in the headspace. The liquid level should also remain low enough such that loss of liquid through the vent to the gas removal pump 117 is prevented. The gas removal pump 117 can induce a vacuum. In certain embodiments, the fluid level sensor 115 can be positioned in either first degassing chamber 103 or recirculating degassing chamber 106 at a location where fluid level sensor 115 is not affected by fluid entering the degassing vessel 100.

To ensure smooth and quiet operation of pumps, a controller can maintain a suitable liquid level in the degassing vessel 100. The controllers can control the valve and pumps wherein fluid is retained at suitable levels inside the degassing vessel 100. The controllers can prevent a pump inlet from being starved of liquid by using sensor inputs such as a tachometer. The recirculating pump 108, gas removal pump 117, and fluid pump 114 can each contain a tachometer depending on the type of pump. For example, a peristaltic or rotary pump can contain a tachometer to measure revolutions per minute (RPM). In other embodiments, a rotary pump with a linear motion piston can also have a tachometer to measure RPM. For example, an increase in a flow rate upstream of the degassing vessel 100 relative to the flow rate downstream of the degassing vessel 100 can increase the liquid level inside the degassing vessel 100. Conversely, a lower flow rate upstream of the degassing vessel 100 relative to downstream can lower the liquid level in the degassing vessel 100. Moreover, a pumping efficiency for certain pumps can decline exponentially as fluid pressure at a pump inlet approaches a high vacuum condition wherein the pump can lose the ability to produce a sufficient fluid pressure differential at the pump inlet to cause filling of the pump mechanism. This inefficiency can be exacerbated when gas bubbles form in a pump inlet to produce cavitation that can reduce fluid outflow. The controller can control liquid levels in the degassing vessel 100 to remain at sufficient levels such that undissolved gas bubbles are separated and captured. The liquid levels can be controlled by a difference between a rate fluid enters the degassing vessel 100 through fluid path 101 and a rate that fluid exits the degassing vessel through the exit line 113. For example, one or more tachometers can read an operating speed of any gear pump. The tachometer can detect an insufficient liquid level in the degassing vessel 100 if a reading from the gas removal pump 117 indicates excessive RPM. Fault conditions that can cause excessive RPM include insufficient liquid level in the degassing vessel 100, excessive foaming, insufficient inlet flow from fluid path 101, or a leak that provides for liquid to bypass the spray nozzle orifices of first sprayer 102 and recirculating sprayer 111. The controllers can detect, monitor, and control the components to avoid the fault conditions.

Proteins and other foam-causing components in the dialysate can generate foam when $CO_2$ bubbles come out of solution in the degassing vessel 100. The foam volume in the degassing vessel 100 can grow proportional to a protein content (and other foam-causing components) to an amount of gas bubbles coming out of solution. The spray rate through the first sprayer 102 and recirculating sprayer 111 can be controlled to provide a dense spray pattern. The dense spray pattern can impinge upon shaped inner surfaces inside the degassing vessel 100. For example, one or more conical upper surfaces can be configured in the first degassing chamber 103 and the recirculating degassing chamber 106 to disrupt an upward growth of foam to form a fluid cap that prevents foam from rising to the top portion of the degassing vessel 100 and passing out through exhaust line 119. If severe foaming occurs, the foam can exit through exhaust line 119, creating an excessive pressure loss. The pressure loss can be detected by a gauge pressure sensor 120, and corrective action taken. The gauge pressure sensor 120 can be positioned in exhaust line 119.

In certain embodiments, the rate of fluid flow through recirculation line 107 can be determined based on a set point dialysate flow rate and an expected sorbent outlet $pCO_2$. The fluid flow through recirculation line 107 can be the degassing loop recirculation flow rate. The degassing loop recirculation flow rate can be controlled by running recirculating pump 108 to achieve a set-point pressure drop across the first sprayer 102 and recirculating sprayer 111 as measured by pressure sensor 122 and gauge pressure sensor 120.

In sorbent-based dialysis, the pressure sensor 122 can measure the pressure at a sorbent outlet and be defined as a Sorbent Outlet Pressure Sensor (SOPS). The pressure sensor 122 can be in fluid contact with the fluid path 101 that receives fluid into the degassing vessel 100. Similarly, the gauge pressure sensor 120 can measure the degassing vessel pressure and be defined as a Degas Vessel Pressure Sensor (DVPS) in sorbent based dialysis. The gauge pressure sensor 120 can be in fluid contact with the exhaust line 119 or vent outlet 133 that exhausts or vents gas during operation from the recirculating degassing chamber 106.

The set fluid pressure differential between the inlets and outlets of first sprayer 102 and recirculating sprayer 111, which is equal to the pressure at pressure sensor 122 and gauge pressure sensor 120, can be determined using an algorithm or lookup table. When the $CO_2$ content of the dialysate is expected to be high, the recirculation rate can be set higher. Conversely, if the $CO_2$ content of the dialysate is expected to be lower, the recirculation rate can be set lower to reduce wear on the recirculating pump 108 and reduce over degassing of the dialysate. In certain embodiments, the dialysate flow rate into and out of the degassing vessel 100 can be set at between 100 mL/min to 600 mL/min. The recirculation rate can be set sufficient that the degassed dialysate exiting at exit outlet 134 is in approximate equilibrium to the gas partial pressure in the headspace. The recirculation rate can also be set to ensure sufficient nozzle pressure so that liquid does not pass thru optional bypass flow path 135 directly from first sprayer 102 to recirculating sprayer 111 without first passing into first degassing chamber 103. The headspace pressure as measured by the gauge pressure sensor 120 and an ambient pressure sensor 121, or an absolute pressure sensor, can be used in combination with the nozzle inlet pressure measured by pressure sensor 122 to set the recirculation rate. The recirculation rate set point based on the pressure sensors can be determined from a lookup table or using a transfer function.

Dalton's law of partial pressures and Henry's law for concentrations of dissolved gasses in solution define the relationship between the degassing vessel 100 headspace pressure and the concentrations of dissolved gases in fluid exiting the degassing vessel 100 when equilibrium is achieved between gases in the liquid and gases in the headspace. Because gas concentrations in liquid at equilibrium are proportional to the absolute partial pressures of the gases in the headspace, the pressure in the degassing vessel 100 can be controlled as an absolute pressure. In certain embodiments, the absolute pressure can be determined using the gauge pressure sensor 120 to measure the gauge pressure in the degassing vessel 100 headspace and an ambient pressure sensor 121. The sum of the gauge pressure as measured by gauge pressure sensor 120 and the ambient pressure as measured by ambient pressure sensor 121 can provide the absolute pressure in the degassing vessel 100 headspace. Alternatively, an absolute pressure sensor can be positioned to take readings in the degassing vessel 100 (not shown). The pressure in the degassing vessel 100 can be controlled by running the gas removal pump 117 and selectively opening and closing valve 118. By raising the pump rate of gas removal pump 117, the pressure in the degassing vessel 100 can be lowered. By lowering the pump rate of gas removal pump 117, the pressure in the degassing vessel 100 can be increased. To avoid operating gas removal pump 117 at a rate below a set minimum rate, valve 118 can be closed when suitable to increase the pressure in the degassing vessel 100. The pressure in the degassing vessel 100 can be set to achieve a specified level of degassing based on an expected inlet carbon dioxide level. Equations to set the headspace pressure can be based on factors such as temperature, inlet $CO_2$, inlet air, and outlet $CO_2$, and can be derived empirically.

To operate the degassing system of the system, the recirculating pump 108 can be set based on the dialysate flow rate and expected carbon dioxide concentration in dialysate entering the degassing vessel 100. The absolute pressure in the degassing vessel 100 headspace can be determined based on the gauge pressure sensor 120 and an ambient pressure sensor 121, or by using an absolute pressure sensor. Once the recirculation rate has been reduced to a minimum suitable rate based on operating conditions, if the headspace pressure is still too high, valve 118 can be opened to provide for gas removal by gas removal pump 117. Once the desired headspace pressure has been reached, the headspace pressure can be controlled using gas removal pump 117 and valve 118 as described.

During priming and draining of the dialysate system, it may be required to provide for air and fluid to enter the degassing vessel 100. Fluid from the dialysate flow path can enter the top of the degassing vessel 100 through exhaust line 119. Fluid can be drawn in through fluid path 128, controlled by valve 124 to enter the degassing vessel 100. Air can be introduced into the system through air filter 125 and enter exhaust line 119 through valve 123 to drain degassing vessel 100.

The degassing vessel 100 can be filled by controlling a dialysate pump to pump fluid into the degassing vessel 100 while fluid pump 114 is either not run or run at a lower rate. To drain the degassing vessel 100, fluid pump 114 can be run to remove fluid from the degassing vessel 100 while any dialysate pumps that would add fluid to the degassing vessel 100 are either not run or operated at a lower rate. Valve 123 can be operated to flow air into the degassing vessel 100 during draining.

Figure 2:
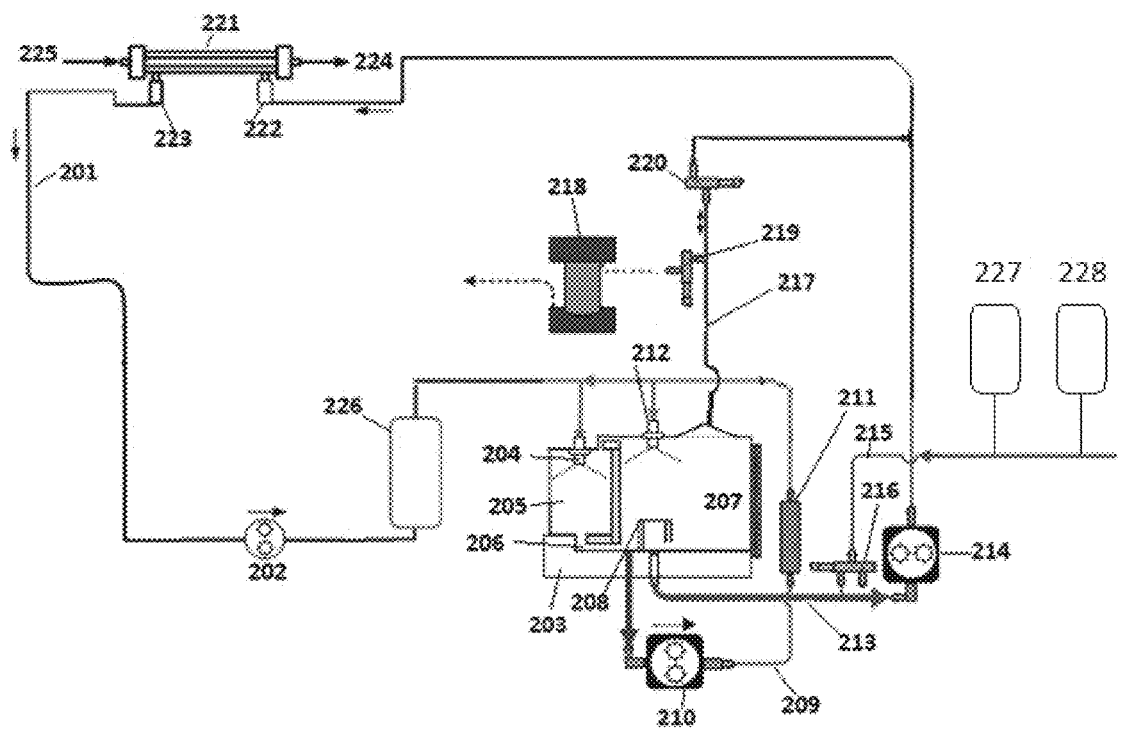
FIG. 2 is a dialysate flow path including a degassing system.

FIG. 2 illustrates a dialysate flow path 201 including a degassing system. The degassing system illustrated in FIG. 2 is simplified and can be the same degassing system as illustrated in FIG. 1A. Dialysate moves through the dialysate flow path 201 from a dialysate outlet 223 of a dialyzer 221 to a dialysate inlet 222 of the dialyzer. Dialysate pump 202 and dialysate pump 214 provide the driving force suitable to move dialysate through the dialysate flow path 201. Blood enters the dialyzer 221 through blood inlet 225 and exits through blood outlet 224. Solutes in the blood move across the dialyzer membrane (not shown) into the dialysate. In certain embodiments, a sorbent cartridge 226 can be included to remove toxins and other solutes from the dialysate. The sorbent cartridge 226 can include urease, which catalyzes the breakdown of urea to carbon dioxide and ammonium ions. The ammonium ions formed can be removed by a cation exchange resin, while the degassing system can remove the generated carbon dioxide.

As described, dialysate can enter a degassing vessel 203 through a first sprayer 204 into a first degassing chamber 205. A portion of the air bubbles and dissolved gases in the dialysate can be removed in the first degassing chamber 205. The dialysate can enter recirculating degassing chamber 207 through fluid channel 206. The dialysate can exit the recirculating degassing chamber 207 through fluid path 209, drawn by recirculating pump 210. In fluid path 209, the dialysate can be heated by heater 211 and recirculated to recirculating sprayer 212, which sprays the dialysate back into the recirculating degassing chamber 207. A portion of the dialysate in recirculating degassing chamber 207 can be drawn out of the recirculating degassing chamber 207 through a second outlet into fluid path 213, drawn by dialysate pump 214 to rejoin the dialysate flow path 201. Baffle 208 can prevent significant amounts of dialysate from entering fluid path 213 without first passing through both the first sprayer 204 and recirculating sprayer 212. A desired headspace pressure is maintained in the degassing vessel 203 by operation of gas removal pump 218 and valve 219, as described with respect to FIG. 1A. The headspace pressure can be controlled to a low pressure (<100 mmHg) and a degas recirculation rate can be reduced to minimize a nozzle pressure (SOPS pressure sensor) so that pressure at the sorbent outlet can be minimized. This control strategy can provide for a liquid flow rate through the sorbent cartridge to be maximized without exceeding a maximum suitable pressure at a sorbent cartridge inlet.

Valve 220 can provide for fluid to be drawn into the degassing vessel 203 through fluid path 217 during priming and disinfection of the system. Bicarbonate from bicarbonate source 227 and cation infusates from cation infusate source 228 can be added to the dialysate flow path 201 through fluid path 215, controlled by valve 216. Pumps and/or valves (not shown) can control addition from the bicarbonate source 227 and cation infusate source 228 to fluid path 215. The additional bicarbonate can create additional carbon dioxide. The system can be set to degas to slightly below the intended carbon dioxide concentration at the dialyzer inlet to compensate for the additional carbon dioxide formed from the bicarbonate addition and acid from the cation infusates. However, the additional carbon dioxide produced is minor relative to the carbon dioxide produced by the conversion of urea and bicarbonate due to the sorbent cartridge. Although shown as a single fluid path 215 for simplicity, one of skill in the art will understand that any number of infusate lines and valves can be included. As described, the degassing vessel 203 headspace pressure is set according to a desired pH and carbon dioxide range, taking into account the bicarbonate and cation infusates added.

Figure 3:
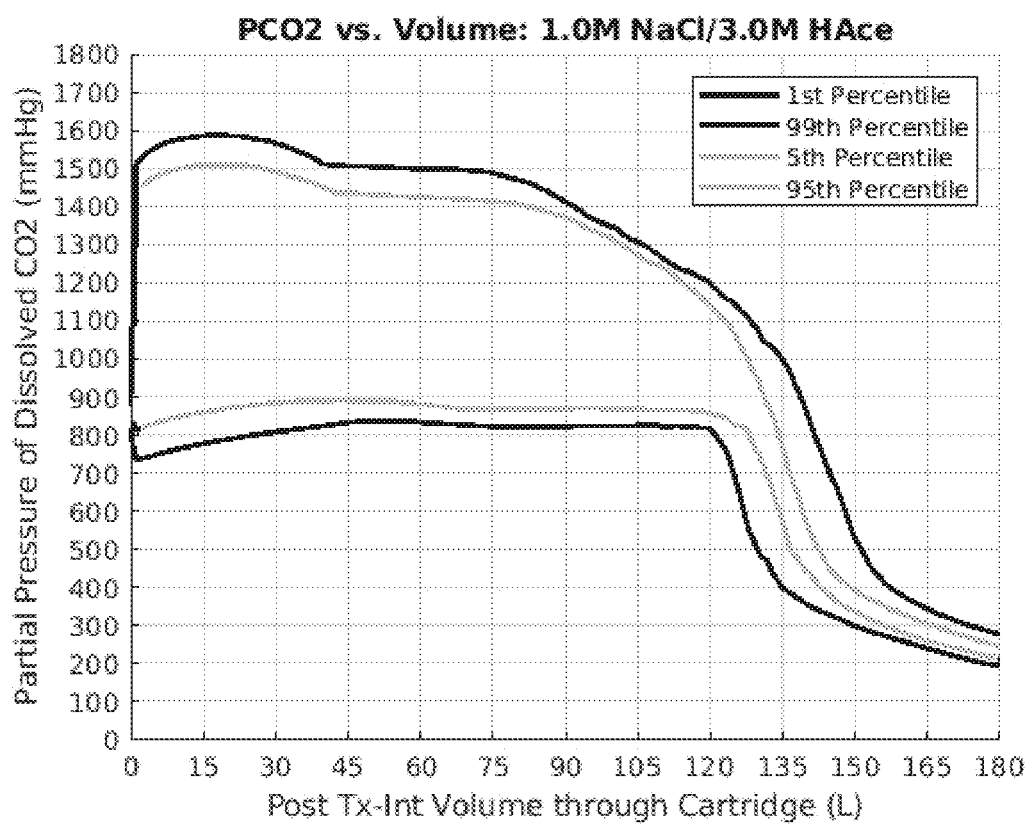
FIG. 3 provides a non-limiting example of expected carbon dioxide concentrations in a dialysate exiting a sorbent cartridge throughout treatment.

As described, the recirculation rate through the degassing system can be set depending on the amount of gas that is needed to be removed from the dialysate and the dialysate flow rate. In certain embodiments, the recirculation rate can be maintained at 1.5× the dialysate flow rate. However, the recirculation rate can be varied depending on the needs of the system and user. The amount of gas that needs to be removed depends on the carbon dioxide concentration in the dialysate entering the degassing system. In systems that use a sorbent cartridge to regenerate dialysate, the amount of carbon dioxide in the dialysate exiting the sorbent cartridge can vary as a function of the sorbent cartridge chemistry, and in particular, a ratio of sodium ions to hydrogen ions bound to zirconium phosphate in the sorbent cartridge. FIG. 3 provides a non-limiting example of carbon dioxide concentration in dialysate exiting the sorbent cartridge as a function of cumulative dialysate processed. The graph in FIG. 3 was created by measuring the carbon dioxide partial pressure in fluid exiting the sorbent cartridge for an inlet solution having 1.0 M NaCl and 3.0 M acetic acid. The data in FIG. 3 is a Monte Carlo simulation based on empirical data and $1^{st}$ principles. FIG. 3 shows possible pressures (amounts) of $CO_2$ throughout a large number of treatment scenarios. The dark lines are what is expected to be seen in 98% of treatments, and the grey lines show what is expected in 90% of treatments. The partial pressure of carbon dioxide in the dialysate exiting the sorbent cartridge decreases as the total volume of dialysate purified by the sorbent cartridge increases because the hydrogen ions in the sorbent cartridge are consumed throughout treatment, raising the pH of the sorbent cartridge and resulting in less $CO_2$ formation. Table 1 summarizes the data from FIG. 3.

TABLE 1

| Volume | Low ($1^{st}$ Percentile) | High ($99^{th}$ Percentile) |
|---|---|---|
| 15 L | 780 mmHg | 1600 mmHg |
| 72 L (12 hr @ 100 mL/min) | 824 mmHg | 1492 mmHg |
| 120 L (4 hr @ 500 mL/min) | 815 mmHg | 1197 mmHg |
| 150 L (250 min @ 600 mL/min) | 299 mmHg | 530 mmHg |
| 180 L (5 hr @ 600 mL/min) | 196 mmHg | 277 mmHg |

In addition to carbon dioxide, the dialysate exiting the sorbent cartridge can include oxygen and nitrogen dialyzed from the patient's blood. Table 2 provides the minimum and maximum expected oxygen and nitrogen in the dialysate exiting the sorbent cartridge for patients with fistula (atrial blood, high dissolved oxygen) or central venous catheter (venous blood, low dissolved oxygen) blood access type, as well as a variety of dialyzers. Various blood and dialysate flow rates are included as the flow rates can influence the amount of gas passed through the dialyzer membrane.

TABLE 2

| Gas Content Scenario | Inputs | | | | | | | | Outputs | |
|---|---|---|---|---|---|---|---|---|---|---|
| | QB (ml/min) | QD (ml/min) | Blood Access | Dialyzer Reference | Ko (ml/min/m2) | A | CBin (mmHg) | CDin (mmHg) | K or D (ml/min) | CDout (mmHg) |
| Low $N_2$ | 50 | 600 | CVC | Baxter CA50 | 262 | 0.50 | 600 | 4 | 46 | 50 |
| Low $O_2$ | 50 | 600 | CVC | Baxter CA50 | 262 | 0.50 | 30 | 1 | 46 | 3 |
| Nominal Case $N_2$ | 300 | 600 | Fistula | Baxter CA-HP 210 | 506 | 2.1 | 600 | 120 | 272 | 338 |
| Nominal Case $O_2$ | 300 | 600 | Fistula | Baxter CA-HP 210 | 506 | 2.1 | 90 | 20 | 272 | 52 |
| High $N_2$ | 500 | 499 | Fistula | B. Braun Xevonta Hi23 | 826 | 2.3 | 600 | 300 | 396 | 538 |
| High $O_2$ | 500 | 499 | Fistula | B. Braun Xevonta Hi23 | 826 | 2.3 | 100 | 50 | 396 | 90 |

Table 2 provides worst case high, low, and medium expected amounts of oxygen and nitrogen present in the dialysate. The amount of oxygen and nitrogen present in the dialysate affects the degasser because if there is more nitrogen and oxygen in the dialysate then $CO_2$ is removed at a less efficient rate since the degasser removes all gasses present in the fluid. The headspace pressure can be controlled taking into account the amount of dissolved nitrogen and oxygen.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be required to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A degasser comprising:
    a degassing vessel having a first degassing chamber and one or more recirculating degassing chambers;
    the first degassing chamber comprising a first sprayer fluidly connectable to a first fluid path for flowing fluid into the degassing vessel, the first sprayer positioned inside the first degassing chamber, a fluid channel positioned inside the first degassing chamber fluidly connected to the one or more recirculating degassing chambers;
    the one or more recirculating degassing chambers comprising a recirculating outlet positioned in the recirculating degassing chamber for recirculating fluid from the recirculating outlet to a recirculating sprayer positioned inside the recirculating degassing chamber, a vent outlet fluidly connected to in the recirculating degassing chamber for venting gas, and an exit outlet for exiting fluid out of the recirculating degassing chamber; and a bypass flowpath fluidly connected to a recirculation line and the first sprayer for flowing fluid from the recirculating degassing chamber back to the first degassing chamber.

2. The degasser of claim 1, further comprising one or more recirculating pumps fluidly connected to the recirculating outlet wherein the one or more recirculating pumps pump fluid to the recirculating sprayer via a recirculation line.

3. The degasser of claim 2, further comprising a heater positioned in the recirculation line or in the first fluid path.

4. The degasser of claim 3, further comprising a temperature sensor positioned in the recirculation line downstream of the heater.

5. The degasser of claim 1, further comprising a gas removal pump fluidly connected to the vent outlet wherein the gas removal pump pumps gas out of the recirculating degassing chamber via an exhaust line during degassing.

6. The degasser of claim 1, further comprising a fluid pump fluidly connected to the exit outlet wherein the fluid pump pumps fluid out of the recirculating degassing chamber via an exit line.

7. The degasser of any one of claims 2 and 5-6, further comprising a tachometer measuring revolutions per minute of the pump.

8. The degasser of claim 1, further comprising a baffle positioned between the fluid channel and the exit outlet.

9. The degasser of claim 1, wherein a nozzle of the first sprayer is more restrictive than a nozzle of the recirculating sprayer.

10. The degasser of claim 1, wherein a nozzle of the first sprayer is less restrictive than a nozzle of the recirculating sprayer.

11. The degasser of claim 1, further comprising a fluid level sensor positioned to measure a liquid level in the first degassing chamber and the one or more recirculating degassing chambers.

12. The degasser of claim 11, wherein the fluid level sensor is a linear array of Hall Effect sensors and a magnetic float.

13. The degasser of claim 1, further comprising a temperature sensor positioned in the first degassing chamber.

14. The degasser of claim 1, further comprising a temperature sensor positioned to measure a temperature in the recirculating degassing chamber.

15. The degasser of claim 1, further comprising at least one pressure sensor; wherein the at least one pressure sensor is configured to determine a headspace pressure of the degassing vessel.

16. The degasser of claim 15, wherein the at least one pressure sensor is selected from the group consisting of a pressure sensor, an ambient pressure sensor, a gauge pressure sensor, and combinations thereof.

17. A method comprising:
flowing fluid from a fluid flow path through the first sprayer into the first degassing chamber of the degasser of claim 1;
flowing fluid from the first degassing chamber into the recirculating degassing chamber; through the first fluid line and through the recirculating sprayer; and
controlling a headspace pressure in the degassing vessel to remove gas from the fluid.

18. The method of claim 17, wherein the controlling the headspace pressure in the degassing vessel comprises controlling a gas removal pump, controlling a valve connecting the gas removal pump to the recirculating degassing chamber, or a combination thereof.

19. The method of claim 17, wherein the headspace pressure is controlled based on a dialysate temperature, a dialysate flow rate through a dialysate flow path, a recirculation rate, and a dialysate carbon dioxide concentration.

* * * * *